US012768847B2

(12) United States Patent
Nair et al.

(10) Patent No.: US 12,768,847 B2
(45) Date of Patent: Oct. 20, 2026

(54) CLOT RETRACTION ASSAY FOR QUALITY MONITORING OF PLATELET PRODUCTS

(71) Applicant: THE GOVERNMENT OF THE UNITED STATES AS REPRESENTED BY THE SECRETARY OF THE ARMY, Fort Detrick, MD (US)

(72) Inventors: Prajeeda M. Nair, San Deigo, CA (US); Andrew P. Cap, Hollywood Part, TX (US); Wayne T. Muraoka, San Antonio, TX (US); James A. Bynum, La Vernia, TX (US)

(73) Assignee: THE GOVERNMENT OF THE UNITED STATES AS REPRESENTED BY THE SECRETARY OF THE ARMY, Fort Detrick (MD)

( * ) Notice: Subject to any disclaimer, the term of this patent is extended or adjusted under 35 U.S.C. 154(b) by 560 days.

(21) Appl. No.: 18/195,111

(22) Filed: May 9, 2023

(65) Prior Publication Data

US 2023/0358769 A1 Nov. 9, 2023

Related U.S. Application Data

(60) Provisional application No. 63/364,387, filed on May 9, 2022.

(51) Int. Cl.
*G01N 33/86* (2006.01)
*B01L 3/00* (2006.01)

(52) U.S. Cl.
CPC ............ *G01N 33/86* (2013.01); *B01L 3/5085* (2013.01); *B01L 2200/16* (2013.01); *B01L 2300/0654* (2013.01); *B01L 2300/0829* (2013.01)

(58) Field of Classification Search
CPC ... G01N 33/86; B01L 3/5085; B01L 2200/16; B01L 2300/0654; B01L 2300/0829; B01L 2300/16
See application file for complete search history.

(56) References Cited

U.S. PATENT DOCUMENTS

| | | | | |
|---|---|---|---|---|
| 8,916,356 | B2 * | 12/2014 | Hemker | C12Q 1/56 435/13 |
| 10,739,358 | B2 | 8/2020 | Pearce et al. | |

(Continued)

FOREIGN PATENT DOCUMENTS

| | | | |
|---|---|---|---|
| DE | 3919559 | C1 | 2/2023 |
| EP | 0932041 | A2 | 1/1999 |

(Continued)

OTHER PUBLICATIONS

Alessi, Marie-Christine et al., "Strenghts and weaknesses of light transmission aggregometry in diagnosing hereditary platelet function disorders", J. Clin. Med., 2020, vol. 9, No. 763, 18 pages.

(Continued)

*Primary Examiner* — Jennifer Wecker
*Assistant Examiner* — Tracy Ching-Tian Colena
(74) *Attorney, Agent, or Firm* — Timothy H. Van Dyke; Wolter Van Dyke; Davis, PLLC

(57) ABSTRACT

This disclosure provides an assay and method for evaluating platelet function by measuring clot retraction in a grooved assay well using light transmittance in a low-volume, microplate formatted assay. The method takes advantage of the ability of platelets to draw the fibrin clot toward one side of the microplate well through an optical light path with readings recorded by a microplate reader. The method is rapid, tractable, has high precision, and yields time-series data that is quantitative. This allows clinicians and transfusion medicine practitioners to perform high throughput platelet function testing in patient samples and in blood/

(Continued)

platelet products. Clot retraction serves as a functional biomarker to determine platelet function by performing the assay in a vessel that is scored to form a groove in which clot retraction occurs. Multiple samples can be tested simultaneously, and optionally an algorithm can be used to extract relevant parameters from the data.

14 Claims, 37 Drawing Sheets

(56) References Cited

U.S. PATENT DOCUMENTS

2007/0060522 A1* 3/2007 Biggerstaff ........ G01N 33/5044 514/19.6
2010/0261211 A1 10/2010 Ataullakhanov et al.

FOREIGN PATENT DOCUMENTS

JP 2002014035 A * 1/2002 ......... G01N 21/6452
WO WO-2018140953 A1 * 8/2018 ........... G01N 21/554

OTHER PUBLICATIONS

Harrison, Paul et al., "Guidelines for the laboratory investigation of heritable disorders of platelet function", British Journal of Haematology, 2011, vol. 155, pp. 30-44.
Holcomb, John B. et al., "The Prospective, Observational, Multicenter, Major Trauma Transfusion (PROMMTT) Study: Comparative Effectiveness of a Time-varying Treatment with Competing Risks", JAMA Surg., Feb. 2013, vol. 148, No. 2, pp. 127-136.
Holcomb, John B. et al., "Transfusion of Plasma, Platelets, and Red Blood Cells in a 1:1:1 vs a 1:1:2 Ratio and Mortality in Patients With Severe Trauma The PROPPR Randomized Clinical Trial", JAMA., 2015, vol. 313, No. 5, pp. 471-482.
Horn, Paul S. et al., "Effect of Outliers and Nonhealthy Individuals on Reference Interval Estimation", Clinical Chemistry, 2001, vol. 47, No. 12, pp. 2137-2145.
Horn, Paul S. et al., "A robust approach to reference interval estimation and evaluation", Clinical Chemistry, 1998, vol. 44, No. 3, pp. 622-631.
Lam, Wilbur A. et al., "Mechanics and contraction dynamics of single platelets and implications for clot stiffening", Nat Mater., Jan. 2011, vol. 10, No. 1, pp. 61-66.
Li, Zida, "A miniaturized hemoretractometer for blood clot retraction testing", Small, Aug. 2016, vol. 12, No. 29, pp. 3926-3934.
Moenen, Floor C. J. I. et al., "Screening for platelet function disorders with Multiplate and platelet function analyzer", Platelets, 2019, vol. 301, No. 1, pp. 81-87.
Munnix, I.C.A. et al., "Harmonizing light transmission aggregometry in the Netherlands by implementation of the SSCISTH guideline", Platelets, 2021, vol. 32, No. 4, pp. 516-523.
Nair, Prajeeda M. et al., "Cold-stored platelets have better preserved contractile function in comparison with room temperature-stored platelets over 21 days", Transfusion, 2021, vol. 61, pp. S68-S79.
Ozarda, Yesim, "Reference intervals: current status, recent developments and future considerations", Biochemia Medica, 2016, vol. 26, No. 1, pp. 5-16.
Tucker, Katherine L. et al., "Clot retraction", Methods Mol Biol., 2012, vol. 788, pp. 101-107.
Varga-Szabo, D. et al., "Calcium signaling in platelets", Journal of Thrombosis and Haemostasis, 2009, vol. 7, pp. 1057-1066.
Reddoch-Cardenas, Kristin M. et al., "Cold storage of platelets in platelet additive solution: an in vitro comparison of two Food and Drug Administration—approved collection and storage systems", Transfusion, 2018, vol. 58, pp. 1682-1688.
Reddoch-Cardenas, Kristin M. et al., "Cold storage of platelets in platelet additive solution maintains mitochondrial integrity by limiting initiation of apoptosis-mediated pathways", Transfusion, 2021, vol. 61, pp. 178-190.
Picker, Susanne M., "In-vitro assessment of platelet function", Transfusion and Apheresis Science, 2011, vol. 44, pp. 305-319.
Getz, Todd M. et al., "Storage of platelets at 48C in platelet additive solutions prevents aggregate formation and preserves platelet functional responses", Transfusion, 2016, vol. 56, pp. 1320-1328.

* cited by examiner

CLOT RETRACTION ASSAY FOR QUALITY MONITORING OF PLATELET PRODUCTS

CROSS-REFERENCE TO RELATED APPLICATIONS

This application is an international application which claims the benefit of U.S. provisional application Ser. No. 63/364,387, filed 9 May 2022. The entire contents of this application is hereby incorporated by reference as if fully set forth herein.

GOVERNMENT FUNDING SUPPORT

This invention was made with government support under grant no. W81XWH-22-0118, awarded by the Department of Defense. The government has certain rights in the invention.

BACKGROUND

1. Field of the Invention

The invention relates to the general field of medicine and medicinal chemistry. In particular, the disclosures here describe an assay useful for quality monitoring of blood products and platelet function testing.

2. Background of the Invention

Platelets play a critical role in promoting hemostasis and reducing blood loss after traumatic injury. Platelets perform this important role by forming stable aggregates, releasing procoagulant factors, adhering to the damaged endothelium, and generating contractile forces to draw the edges of damaged tissues together. Acquired coagulation disorders in trauma patients can reduce the body's ability to form stable clots and stop bleeding. Platelet dysfunction is particularly detrimental in these disorders as the interaction of platelets with endothelium and coagulation factors is crucial to promote stable clot formation at the injury site. Accordingly, platelet transfusions significantly improve the hemostatic outcome in actively bleeding patients.

Activated platelets that are incorporated into a clot engage fibrin through specific ligand-receptor interactions (e.g., $\alpha_{IIb}\beta_3$) and begin to contract their cytoskeletons, leading to clot retraction. This process compacts the fibrin fibers into a tight "mesh-like" network and increases clot strength to provide structural stability and to re-approximate damaged tissue margins. In the process, excess fluid is expelled and the clot size is reduced. Clot retraction requires platelet activation, fibrin(ogen) engagement, cell signaling (e.g. Src-family kinase), actin rearrangement, and is energetically intensive.

The current methods to evaluate clot retraction require large sample volumes (about 1 mL) and the results are qualitative and subject to interpretation when clot weights are measured. Despite the need for quality monitoring of platelet products and platelet function testing, the current methods to evaluate platelet function are expensive, cumbersome and low-throughput. They require large sample volumes and an advanced lab setting for performance and interpretation. Additionally, the conventional platelet assays fail in providing a comprehensive assessment of its function, which is partially due to the lack of an established all-inclusive platelet functional marker.

Information about platelet metabolism and signaling is limited in prior art platelet function tests. Thromboelastography, for example, is low throughput and measures clot properties; information about platelets may be missed. Light transmission aggregometry is susceptible to analytical variables, requires high sample volume, and is manual and time-consuming. Platelet contraction assays require all aspects of cell physiology in order to successfully cause clot retraction. Unfortunately, these current methods to measure clot retraction do not provide quantitative measurements, and results are subject to interpretation or are merely binary (retraction/no-retraction). Currently, there are no commercial instruments or assays that can quantitatively measure clot retraction.

Dynamic measurements of clot retraction by time-lapse imaging require sophisticated equipment and intensive image analyses. Other methods to evaluate clot retraction using strain sensors also require image acquisition and processing, making the test low throughput. In all, platelet function testing is limited by the requirement of large sample volumes, specialized equipment, and/or data analyses, and would benefit from a method that can test multiple samples simultaneously and can be performed using common laboratory equipment.

Storage of platelet products is known to result in a progressive decline in platelet function which may adversely impact the product's hemostatic capability. In vitro functional testing of platelets can aid in the identification of specific platelet units and donors that have the characteristics that are desirable for transfusion and identify those with platelet dysfunction. Additionally, platelet function testing can aid in monitoring patients at risk of bleeding due to surgical complications or who are at risk of thrombosis. Therefore, there is a need in the art for high-throughput methods to analyze both patient samples and platelet products for platelet function to identify patients and specific platelet units or blood products that are deficient in platelet/clotting function.

SUMMARY OF THE INVENTION

Thus, the present disclosure presents a reliable and consistent assay for clot retraction, which can be used as comprehensive biomarker of platelet function. This method addresses the issues concerning the conventional platelet tests which fail to provide a comprehensive assessment of platelet function and only capture information about adhesion or aggregation.

In particular embodiments, the present invention relates to a microplate for reading in a microplate reader comprising a series of wells that have been coated with an anti-adherent substance that prevents clot adhesion to the surface and a scored mark on the side of the well in a position so as to be measurable through the optical light path of the detection device. Other embodiments pertain to a kit comprising the microplate. The kit may include one or more of instructions for performing a clot retraction assay, a thrombin stock solution, a $CaCl_2$) solution, platelet-poor plasma, buffers, and a hand-held or table-top light transmittance detection device.

Another embodiment is a method for determining platelet function in a platelet sample based on the calculation of the rate of clot formation or the maximum clot retraction. The method involves (a) adding a thrombin solution to the assay vessel under conditions to allow clotting of the sample to occur; (b) mixing a solution containing calcium with a sample containing platelets to be assayed to calcify the platelets; (c) adding the calcified platelets to the assay vessel to initiate clotting and immediately begin light transmittance detection of the sample in the assay vessel, taking periodic readings of light transmittance over a period of about 30 minutes; and (d) determining the rate of clot formation or maximum clot formation for the sample, wherein the interior of the assay vessel is coated with an anti-adherent substance and wherein a portion of the interior side of the assay vessel comprises at least one groove where clot retraction can take place in a position such that the clot retraction is detectable by light tramsmittance. In specific examples, the platelet sample is a clinical sample or a stored platelet product. In a more specific example the platelet sample contains about $1\times10^8$ to about $3\times10^8$ platelets/mL. In other specific examples, the thrombin solution contains about 0.5 to about 3 U/mL thrombin. The anti-adherent substance may be a reagent that affects the surface property of the test chamber to allow clot retraction.

In other embodiments, provided is a method for determining platelet function in a platelet sample based on the calculation of the rate of clot formation or the maximum clot retraction. The method involves (a) placing 5 μL of a 30 U/mL thrombin solution into a well of a 96-well microplate; (b) placing the microplate into a spectrophotometer; (c) preparing a platelet sample containing $2.5\times10^8$ platelets/mL and 6 mM $CaCl_2$) and placing 180 μL of the sample in the well with the thrombin to initiate clotting; (d) immediately begin light transmittance detection of the sample in the assay vessel, taking readings of light transmittance every 5 seconds over a period of about 30 minutes; and (e) determining the rate of clot formation or maximum clot formation for the sample, wherein the interior of the assay vessel is coated with an anti-adherent substance and wherein a portion of the interior side of the assay vessel comprises at least one groove where clot retraction can take place in a position such that the clot retraction is detectable by light transmittance.

BRIEF SUMMARY OF THE DRAWINGS

Certain embodiments are illustrated by way of example, and not by way of limitation, in the figures of the accompanying drawings.

FIG. 8A presents representative time-series O.D. values (red traces) and end-point well scan (blue heatmap) which shows the position and size of the clot 30 min after initiating the reaction. FIG. 8B through FIG. 8G are a series of barplots of six parameters that were extracted from the time-series data as indicated.

FIG. 9A presents representative time-series O.D. values (red traces) and end-point well scan (blue heatmap) which shows the position and size of the clot 30 min after initiating the reaction. FIG. 9B through FIG. 9G are barplots of six parameters that were extracted from the time-series data as indicated.

FIG. 11A is a representative time-series O.D. values (red traces) and end-point well scan (blue heatmap) which shows the size and position of the clot 30 min after initiating the reaction. FIG. 11B through FIG. 11G are barplots of six parameters that were extracted from the time-series data.

FIG. 12A is a representative time-series O.D. values (red traces) and end-point well scan (blue heatmap) which shows the size and position of the clot 30 min after initiating the reaction. FIG. 12B through FIG. 12G are barplots of six parameters that were extracted from the time-series data.

FIG. 14C, FIG. 14D, and FIG. 13E are graphs showing weak correlation of the same parameter using different agonists.

Figure 18A:
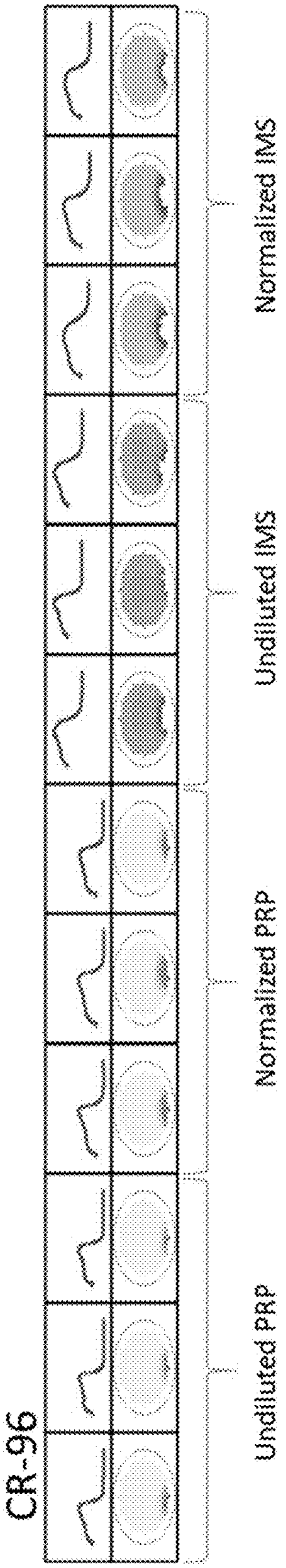
FIG. 18A and FIG. 18B show two different assay results using platelet samples prepared using immunomagnetic separation (IMS) versus traditional centrifugation (PRP) for undiluted and normalized count samples.
Figure 18B:
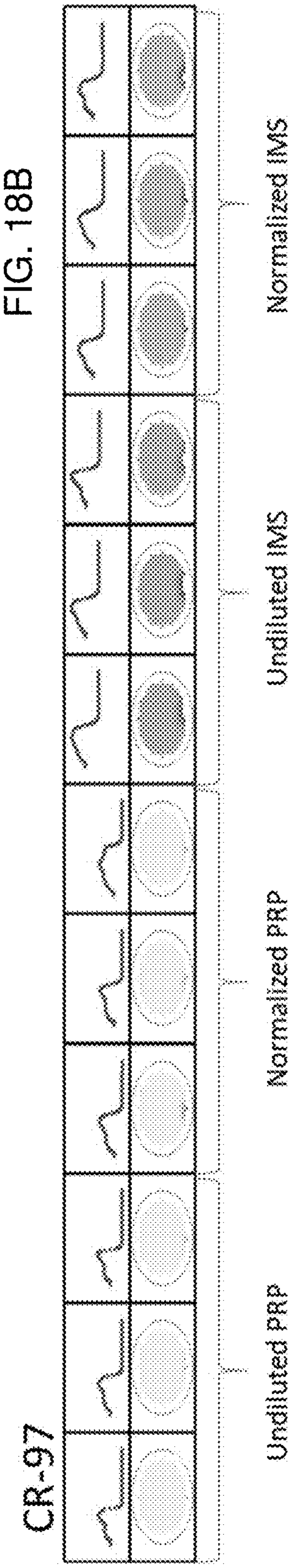

Results are shown in FIG. 18 and indicate that IMS preparation

Figure 19:
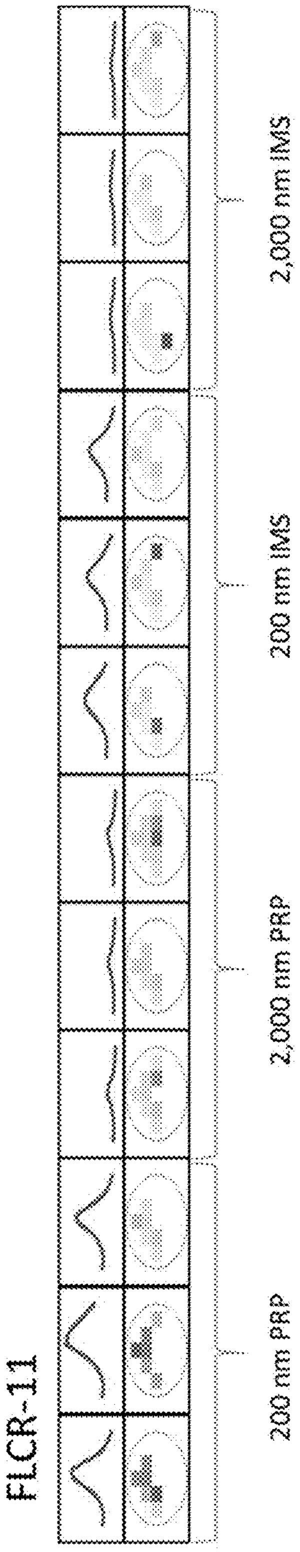

FIG. 19 shows that fluorescence detection identified clot formation and clot retraction that resembled visible light transmission.

DETAILED DESCRIPTION OF EMBODIMENTS OF THE INVENTION

1. Definitions

Unless defined otherwise, all technical and scientific terms used herein have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

All publications, patent applications, patents, and other references mentioned herein are incorporated by reference in their entirety. In case of conflict, the present specification, including definitions, will control. In addition, the materials, methods, and examples are illustrative only and not intended to be limiting.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

As used herein, the term "about" means plus or minus 20 percent of the recited value, so that, for example, "about 0.125" means 0.125±0.025, and "about 1.0" means 1.0±0.2. Notwithstanding that the numerical ranges and parameters setting forth the broad scope of the invention are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

As used herein, the term "blood product" refers to stored or collected blood, plasma, serum, erythrocytes, any purified, semi-purified, or mixed blood cells (e,g., peripheral blood mononuclear cells), platelets, or any sub-portion of blood.

As used herein, the term "platelet product" is a type of blood product that contains purified or semi-purified platelets (e.g., platelet rich plasma or stored platelets for transfusion).

As used herein, the term "platelet sample" refers to platelets derived from a blood patient sample.

As used herein, the terms "subject," "individual," "host," and "patient," are used interchangeably to refer to any animal, and can include humans, simians, avians, felines, canines, equines, rodents, bovines, porcines, ovines, caprines, mammalian farm animals, mammalian sport animals, and mammalian pets. A preferred subject is a human patient. A "subject in need" refers to a subject or patient suffering from trauma or an episode involving bleeding or likely to be suffering from such a condition, for example a patient scheduled for surgery or employed in a dangerous occupation. This term also refers to a subject who has donated blood or platelets for transfusion, or intends to do so.

As used herein, the term "austere environment" refers to a location away from the facilities of medical or clinical laboratories such as a battlefield, accident scene, disaster area, remote or rural location, and the like.

As used herein, the term "score" refers to creating a groove, trench, furrow, or the like using a needle or like sharp instrument, such as an 18 gauge hypodermic needle, on the side of the well or container in which the assay is conducted. The groove is placed such that the detecting device (i.e., spectrophotometer) can read or detect this area of the well or container to measure clot retraction in the groove.

As used herein, the term "groove" refers to the scored mark created on the container in which the clot retraction assay is performed.

2. Embodiments of the Invention

A. Introduction

References are made herein in detail to various exemplary embodiments, examples of which are illustrated in the accompanying drawings. It is to be understood that the following detailed description is provided to give the reader a fuller understanding of certain embodiments, features, and details of aspects of the disclosure, and should not be interpreted as a limitation of the scope of the disclosure.

B. Assay

1. General Discussion

The function of platelets is to adhere, aggregate, and contract for optimum retraction, supported by robust platelet bioenergetics that exert potent contractile forces to remodel and compact the fibrin structural scaffold through the dynamic platelet cytoskeleton. Clot retraction (CR) has been identified here as a unique all-encompassing platelet functional marker that can be used as a proxy for total platelet function.

This invention takes advantage of ability of platelets to pull away from test tubes or other containers for assay after clot initiation to create a simple and easy-to-use benchtop assay to evaluate and quantify CR in a multi-well plate using a plate reader or other similar system as known in the art. This CR assay is useful for testing clinical samples from a patient or a platelet donor, and to test the viability of stored platelets. Each of these uses can guide important transfusion related decisions for the treatment of trauma patients, especially where there is a need to reduce the operational logistical burden and increase survivability.

Here, we describe a multi-well based microplate a clot retraction assay method that requires a relatively short runtime and small sample volume. The method involves continuous optical density monitoring of platelet rich plasma that is activated with thrombin to begin clot formation within a groove scored in the well or other container in which the assay is performed. The data from the method can be analyzed using time-series analytical tools to generate quantitative information about different phases of clot formation and clot retraction. The method demonstrated good repeatability and reproducibility, and is robust to different calcium concentrations. Impairment of platelet bioenergetics, actin polymerization, fibrin interaction, and signaling all significantly affect CR and are detected by the new method. The method showed good agreement with the prior art method of light transmission aggregometry, showing that clot retraction is predictive of platelet function.

In preferred embodiments of the invention, the CR assay involves preparing a well or other container which is coated with one or more substances that prevent or greatly retard adhesion of clots to the surface and then creating a groove by scratching the surface with a narrow, sharp instrument such as a hypodermic needle. When the sample to be tested is whole blood, platelet rich plasma (PRP) is produced by centrifugation; if the sample is apheresis platelets or is otherwise already purified, no further preparation of the sample is necessary. A further centrifugation step is used to produce platelet poor plasma (PPP) from the sample or PPP is provided to the user as part of a kit for the assay.

To perform the assay itself, thrombin solution is placed in the prepared well or container. Then appropriate volumes of the PRP sample or stored platelet sample (diluted if necessary with PPP to achieve a final platelet concentration for assay) are added to the well. To adjacent wells, $CaCl_2$ solution is added to be used to recalcify the PRP. The microplate, well, or other container is placed into the detection device, for example a spectrophotometer and the calcium solution is added to the scored assay wells. Readings for detection are begun immediately and continued for about 30 minutes at intervals of about 5 seconds.

2. Specialized Reagents

The specific reagents used in embodiments of the inventive CR assay include a 1 M $CaCl_2$) stock solution in water, preferably ultrapure water, which can be stored in aliquots at −20° C. for about 6 months. A thrombin solution at 30 U/mL also is prepared by serial dilution in phosphate buffered saline (PBS) and stored on ice. Those skilled in the art will appreciate that concentration of thrombin can be adjusted. In certain embodiments, the thrombin solution can be about 0.5 U/mL to about 3 U/mL. Because the assay performance is affected by thrombin concentration, it is highly preferable that the method is performed using thrombin within the ranges provided above.

Platelet poor plasma can be prepared from a blood sample being tested or can be prepared and provided separately. An anti-adherence rinse solution (AARS) also is prepared or obtained commercially. This solution contains surfactants, or alternatively can contain detergents, proteins and salts. Preferably, the AARS can be obtained commercially, for example from Stem Cell Technology 3. Specialized Equipment The assays according to embodiments of the invention are performed in a well, test tube, or other container. For simplicity, the term "well" will be used here to refer to any suitable container as known in the art. In preferred embodiments, the assay is conducted in a multi-well plate, such as a 96-well plate, to allow multiple samples to be processed at once for high throughput.

The wells of the plate in which the assay is to be conducted are prepared by coating the wells with a solution that prevents adherence to the surface of the well. For example, a microtiter plate can be centrifuged for about 5 to 10 minutes at ambient temperature at about 1000 to about 1500 RCF and most preferably for about 1300 RCF at maximum acceleration and maximum brake for about 10 minutes. After coating, the wells preferably are aspirated and then rinsed with PBS or another suitable buffer that does not contain calcium.

Figure 1B:
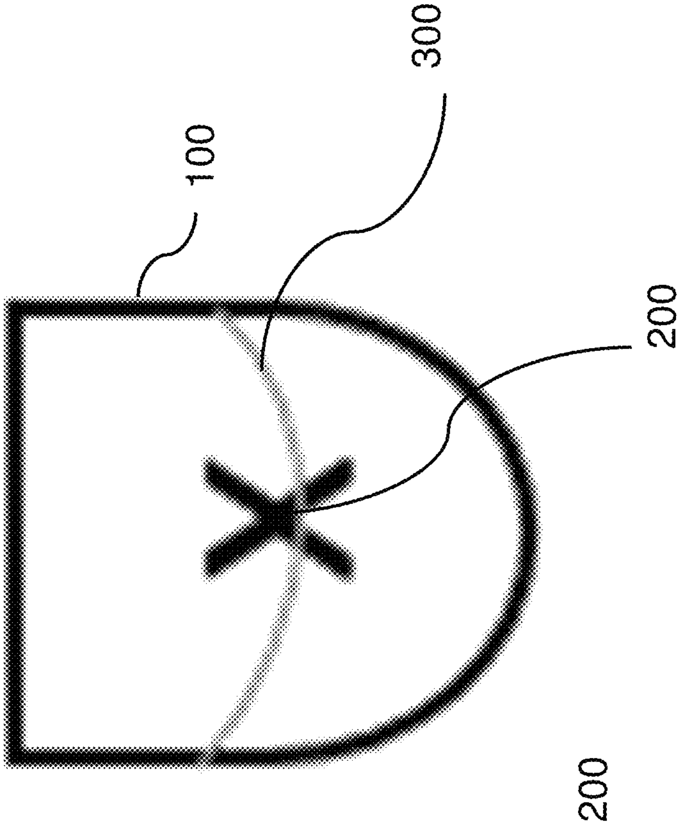
FIG. 1A and FIG. 1B are drawings showing top (FIG. 1A) and side (FIG. 1B) views of a microplate well 100, showing the location of the groove 200 in the well 100 at the position of the meniscus 300 of the fluid for the assay.
Figure 1A:
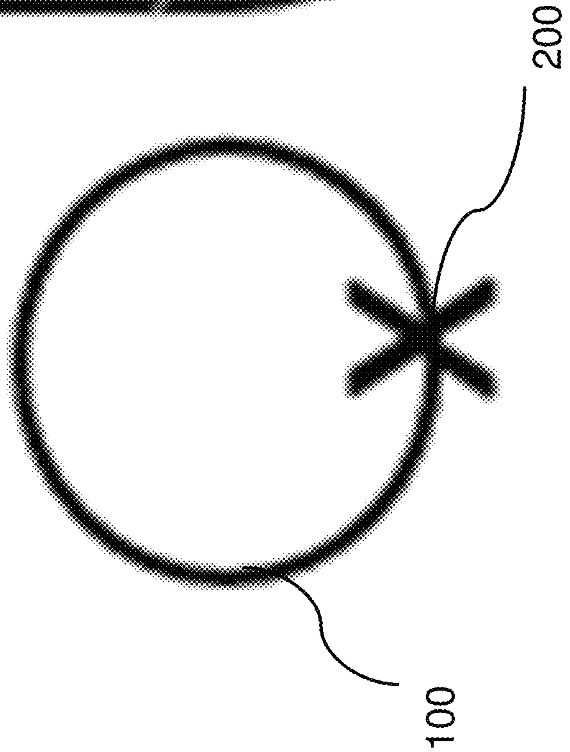

The coated wells are then scored to produce a groove on the side of the well in a position such that the detection device will detect the clot retraction, which occurs in the groove. See FIG. 1. In preferred embodiments, the groove is located in the 6 o'clock position on the side of the well at the level of the meniscus when all reagents are contained in the well and forms an "X." The groove preferably is about 2-5 mm in diameter and is deep enough to cause stable clot attachment upon retraction.

The detection device can be a spectrophotometer microplate reader or other similar device for detection of visible light or fluorescence so as make kinetic measurements over a certain wavelength and time. In certain embodiments, the CR assay uses a multi-well microplate reader for high throughput sample testing. Another option is a portable, hand-held device for single sample testing which can be used bedside and/or in the field. In another embodiment, the method uses fluorescent detection of clot retraction. Fluorescent detection has advantages over visible light detection as the excited and measured wavelengths can be fine-tuned in order to produce data that has less noise in the presence of hemolyzed red blood cells.

Other general laboratory equipment is used in preferred embodiments, such as a benchtop centrifuge, an automated cell counter, a vacuum aspirator, and suitable pipettes and pipette tips.

C. Samples and Sample Preparation

Samples suitable for use with embodiments of the invention include any blood product containing platelets, whether obtained directly as a clinical patient sample or in a blood bank setting. Preferably, the samples are platelet products or whole blood.

If the sample is whole blood, PRP is prepared from the blood, by centrifugation or any other means known in the art. Such methods are familiar to the person skilled in the art. The PRP is diluted with PPP to produce a sample containing about 100,000 to about 500,000 platelets per microliter, or about $2.5\times10^8$ platelets per mL for assay. Platelets that are already separated from other blood components such as erythrocytes and other blood cells need no further processing except dilution to achieve the concentration of platelets above. Thrombin and platelet concentrations have a larger effect on the clot retraction assay method, therefore the assay preferably is performed on samples within the ranges provided above.

In testing stored apheresis platelets in a blood bank setting, the inventive microplate clot retraction method was able to detect a significant difference in the function of platelets stored in autologous plasma compared with platelet additive solution after seven days of room temperature storage. This assay method therefore is useful in improving collection and storage of platelet products by determining the effect of different banking protocols on the function of the products, and to increase quality control in blood banking facilities. In testing patient samples, the CR assay method can determine if a prospective surgery patient is likely to exhibit decreased clotting function, for example, and explain prolonged bleeding in an injured patient.

The method is based on the ability of platelets to draw the fibrin clot toward one side of the microplate well through an optical light path with readings recorded by a microplate reader over time. The method is rapid, tractable, has high precision, and yields time-series data that is quantitative.

D. Results

Data obtained from the assay includes the rate of clot retraction and the maximum clot retraction. The degree of platelet activation and contraction is quantitated in a sample of platelet rich plasma from a patient sample or from platelet products for use in transfusion. The assay is based on kinetic measurement of light transmittance over time in a well, and particularly in a groove in the well where clot retraction can occur in a specific location that is subject to light transmittance detection. The scored area of the well is a surface on which the clot can attach and the direction in which the clot will retract.

In performing the inventive methods according to certain embodiments, platelet rich plasma from the sample to be tested is added to the prepared well and the clotting reaction is initiated. Optical density measurements are taken in intervals (e.g., five second intervals for a duration of 30 minutes). The method yields data that can be analyzed using time-series algorithms for automated data analyses. Automated data mining tools that use freely available software were developed to extract relevant parameters from time-series data.

In addition to the clot retraction assay itself, we have developed an automated scripting procedure in R software that extracts relevant parameters from the data and yields quantitative information about clot formation and clot retraction. All extracted parameters can be analyzed using traditional statistical tools, however.

The microplate clot retraction method yields quantitative insight into several phases of clot formation and retraction. The method has high repeatability and reproducibility, there was little skewness among healthy donors, and the coefficient of variation was in line with commercial LTA and Multiplate devices. The presence of few outliers suggest individual differences among our donor population. There were notable differences in parameters associated with clot retraction (e.g., Rate of Retraction, Retraction Coefficient, Time to Max. O.D., and Retraction Time) when platelet function was antagonized through pharmacologic inhibition, indicating that the method is able to detect various platelet dysfunctions. In addition, the method was able to distinguish between the function of plasma- and PAS-stored platelets, suggesting improved function in the PAS-stored platelets. This finding is in line with prior reports using a variety of methods. In all, the microplate clot retraction method overcomes the limitation of testing samples individually in specialized devices, while producing quantitative data for various phases of clot formation and clot retraction.

E. Uses

The CR assay embodiment comprising a multi-well format is able to draw more in-depth inferences about the blood hemostatic potential of products compared to current clinical standards due to its ability to capture the effects of several phases of platelet-fibrin interaction during coagulation. Hence, this assay can serve as a better diagnostic method for guiding clinical transfusion practice.

One use of this assay method is to monitor platelet function in blood and platelet products during manufacture and storage in blood banks. This method can also be translated to cost effective biosensors that can be used in emergency medical services, surgical suites, mobile medical facilities, disasters, accident scenes, and other austere environments to evaluate patients for platelet dysfunction, an indicator of acute traumatic coagulopathy. Other clinical uses are screening for presurgical bleeding risk and monitoring patients on (anti) platelet therapies, as well as testing actively bleeding patients.

F. Kits

Embodiments of the invention include kits for performing the CR assay, either in a hospital or other clinical or laboratory setting, or in the field. Such kits contain at a minimum one or more prepared microplates or other suitable container(s) for the assay. The plates, wells, or containers have been prepared by coating and scoring as described herein. Preferably, the plates are in a sealed container and can be stored at room temperature and ambient humidity for up to 12-18 months. Preferably, the kit also contains instructions for performing the assay, including sample preparation.

In certain embodiments, the invention provides a ready-to-use kit, for off the shelf use in hospitals, clinics, blood banks, and the like or for field use in austere conditions such as the battlefield, accidents, disaster locations, and the like. The kits preferably contain a microplate, such as a 96-well plate, or any container with wells or any container suitable for performing the assay. The container is prepared by coating and scoring as described herein and can be stored at ambient temperature and humidity, preferably in a sealed container such as a box, pouch, or the like.

Optionally, the kits also contain an alternative means for preparation of platelet rich plasma for use in austere environments so that the platelet rich plasma does not need to be prepared on site. Such means include, but are not limited to Blood filters.

In some embodiments, the kits also contain one or more of a thrombin stock solution, platelet poor plasma, a $CaCl_2$) solution, buffers, and/or a hand-held or table-top detection device. These components are packaged together for ease of use in the field or in a laboratory setting.

G. Conclusion

As noted above, blood platelets are crucial to prevent excessive bleeding following traumatic injury. Accordingly, platelet transfusions significantly improve the hemostatic outcome in actively bleeding patients. However, the manufacture and storage of platelet products for transfusion leads to a decline in platelet function. This method is advantageous in that it is a low sample volume and high throughput method which can be used to screen donors and platelet products for dysfunction(s) prior to product release to hospitals or use in patients.

The method entails, in a broad embodiment, in a well or assay container, adding thrombin to platelet rich plasma, under conditions which allows clotting to occur. One portion or part of the interior of the well or container is scored so as to form a groove that can accommodate fibrin clot retraction so as to be measurable through the optical light path of the detection device. The interior is preferably scored prior to addition of the thrombin and plasma. Optical density is measured in intervals, and data is analyzed using time-series algorithms. The method is based on the ability of platelets to draw the fibrin clot toward one side of the microplate well through an optical light path with readings recorded by a microplate reader.

The inventive method, in its simplest embodiment, measures clot retraction using light transmittance in a low-volume, multi-well format assay. In some embodiments the assays use 96-well microtiter plate, but as it would be clear to someone having skill in this art, any size or number of wells can be used as is convenient. In all, this method provides clinicians and transfusion medicine practitioners with the ability to perform high throughput platelet function testing using low volume samples to yield consistent, reproducible results with commonly available laboratory equipment. The method provides quantitative information and avoids subjective interpretation.

3. Examples

This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Although any methods and materials similar or equivalent to those described herein can be used in the practice or testing of embodiments of the present invention, the preferred methods, devices, and materials are now described. All publications mentioned herein, are incorporated by reference in their entirety; nothing herein is to be construed as an admission that the invention is not entitled to antedate such disclosure by virtue of prior invention.

Example 1. Standardized Protocol for Microplate Clot Retraction Assay

A Introduction.

This example provides a detailed procedure using the BioTek Synergylneo2 spectrophotometer and Gen5 software; however, other makes and models of spectrophotometers can be used within the assay parameters, as would be understood by someone having ordinary skill in this art. Well-known substitutions for certain equipment and reagents also are known in the art and are considered suitable for use with the invention. Platelets are thought to be sensitive to shear stress and temperature fluctuations. Specimens should be collected carefully and handled properly to ensure accurate results.

TABLE 1

Abbreviations, Acronyms, and Terms.

| Identifier | Description |
|---|---|
| ACD-A | Acid Citrate Dextrose Solution A |
| PRP | Platelet Rich Plasma |
| PPP | Platelet Poor Plasma |
| Q.S. | Quantum Satis (as much as suffices) |
| RBB | Research Blood Bank |
| RCF | Relative Centrifugal Force |
| RT | Room Temperature |

B. Materials and Equipment.

1. Freshly drawn whole blood or PRP sample with acid citrate dextrose (ACD-A) as anticoagulant.
2. 1.5 ml centrifuge tubes (VWR Cat #10025-722)
3. 15 ml conical tubes (Nunc Cat #339560)
4. 96-well Microtiter Microplates (Nunc Cat #2205)
5. 18 Ga needle
6. Anti-adherence Rinse Solution (Stem Cell Technology Cat #7010)
7. Phosphate Buffered Saline (Gibco Cat #20012-027)
8. Calcium chloride (Sigma Cat #C1016)
9. Human alpha thrombin (Haematologic Technologies Cat #HCT-0020-1 MG)
10. Benchtop centrifuge capable of 3,000 RCF with swinging bucket rotor
11. Automated cell counter (i.e., Advia, Horiba Micros 60)
12. Microplate reader (i.e., BioTek Synergylneo2)
13. Vacuum aspirator
14. 1000 μl pipette and tips
15. 200 μl single channel and multichannel pipette and tips C. Procedure.

1. Prepare a 1 M Calcium Chloride ($CaCl_2$)) stock solution: Weigh 1.1 g calcium chloride and Q.S. to 10 ml with ultrapure water. Aliquot to sterile 1.5 ml tubes. Label and date tubes. Store aliquots at −20° C. The solution expires after 6 months.
2. Obtain whole blood or apheresis platelets collected in Acid Citrate Dextrose (ACD-A) tubes (yellow top).
3. Assay parameters: Temperature: 37° C.; Assay duration: 30 minutes; Read interval: 5 seconds; Kinetic absorbance wavelength: 350 nm; Well scan absorbance wavelength: 350 nm.
4. Prepare Platelet Rich Plasma (PRP) if starting material is whole blood. If starting material is apheresis platelets, this section can be skipped.
   a. Centrifuge the ACD-A tubes for 10 min, 200 RCF, 22° C., max acceleration, no brake.
   b. Remove the stopper on the ACD-A tube and transfer the top layer of plasma and platelets to a 15 ml tube using a 1000 μl pipette. Stop aspirating when approximately 200-300 μl of plasma is left to avoid transfer of undesired cells.
   c. Label the 15 ml tube "PRP" and keep at Room Temperature (RT). Replace the stopper on the ACD-A tube.
   d. Obtain platelet counts of the "PRP" tube using an automated cell counter (Advia, Horiba Micros 60, etc).
5. Prepare Platelet Poor Plasma (PPP)
   a. Centrifuge ACD-A tubes 3,000 RCF for 10 min, 22° C., max acceleration, max brake.
   b. Remove the stopper on ACD-A tube and transfer the top layer of plasma to a 15 ml tube using a 1000 μl pipette. Stop aspirating when approximately 200-300 μl of plasma is left to avoid transfer of undesired cells.
   c. Label this 15 ml tube "PPP" and keep at RT.
6. Prepare the 96-well microplate
   a. Determine the number of wells that will be required for the test allowing for 3 technical replicates of each sample, i.e., (number of samples)×3=number of wells required. Control wells could be prepared by wells with no grooves and just by coating with anti-adherence rinse solution. This would provide a clot curve but will not cause retraction.
   b. Coat wells by adding 150 μl Anti-adherence Rinse Solution to each well that is needed to complete the test.
   c. Centrifuge the plate 1,300 RCF for 10 min, 22° C., max acceleration, max brake.
   d. Aspirate the Anti-adherence Rinse Solution with a vacuum aspirator.
   e. Wash wells by adding 200 μl Phosphate Buffered Saline (PBS) to each coated well. It is important that the PBS does not contain calcium.
   f. Aspirate PBS from the wells using a vacuum aspirator.
   g. Score the 6 o'clock position of each coated and washed well with an 18 Ga needle in an "x" pattern at the level of the meniscus when sample is contained in the well. See FIG. 1 for an illustration showing top (FIG. 1A) and side (FIG. 1B) views of a scored well. The X 200 indicates the location of the groove on the well 100, which is located at the level where the meniscus 300 is when sample is added to the well.

7. Prepare working thrombin solution
   a. Record the lot number, specific activity, and concentration of the stock thrombin tube, and calculate the thrombin activity in U/mL using the following equation:

$$\text{Thrombin activity } (U/mL) = \text{Specific Activity } (U/mg) \times \text{concentration } (mg/mL).$$

b. Prepare a working thrombin solution of 30 U/ml by serially diluting in PBS. Keep working thrombin solution on ice.
8. Transfer 5 μL of working thrombin solution (30 U/ml) to each microplate well to be tested.
9. Dilute and re-calcify PRP
   a. Calculate the volume of PRP, PPP, and $CaCl_2$) needed for each sample.

$$PRP\text{ volume } (\mu l) = \frac{\text{final platelet concentration } \left(\frac{K}{\mu l}\right) \times \text{reaction volume } (\mu l)}{\text{platelet concentration } \left(\frac{K}{\mu l}\right)}$$

b. The standardized method uses final platelet concentration=250 and reaction volume=600

$$\text{CaCl2 Correction factor} = \left(\frac{\text{reaction volume } (\mu l)}{145}\right) \times 5$$

c. The standardized method uses reaction volume=600

$$\text{CaCl2 } (\mu l) = \frac{\text{desired Calcium concentration (mM)}}{1000} \times \frac{\text{reaction volume } (\mu l)}{1000} \times 1000$$

d. The standardized method uses desired Calcium concentration=6 and reaction volume=600
      PPP volume (μl)=
      =reaction volume—PRP volume
      —$CaCl_2$) Correction factor—Ca
10. Combine the appropriate volumes of PPP, PRP, and $CaCl_2$) in a 1.5 ml tube.
11. Transfer 180 μl of the re-calcified PRP to wells adjacent to the wells containing thrombin.
12. Place the microplate into the spectrophotometer.
13. Using a 12-channel pipette, transfer 145 μl of the re-calcified PRP to the well that contains thrombin. Simultaneously, press the run button in the Gen5 software to initiate the run. After the run has completed, the plate will eject from the spectrophotometer. Discard the plate in the appropriate receptacle.
14. Export the raw data in text format by selecting the plate in the menu tree and right click for a menu that offers File Export options.

Example 2. Clot Retraction Assay for Monitoring of Platelet Products

A. Platelet Preparation.

Whole blood was collected in acid citrate dextrose tubes (ACD-A; BD Vacutainer, Franklin Lakes NJ) from healthy volunteers in accordance with a U.S. Army Research and Development Command approved protocol (USAISR L-20-003). Whole blood was centrifuged at 200×g for 10 minutes and platelet rich plasma (PRP) was obtained from the upper layer. Platelet poor plasma (PPP) was recovered from the remaining volume of the ACD-A tube after centrifugation at 3,000 times gravity (xg) for 10 minutes. To obtain apheresis platelets, the Trima Accel 7 (Terumo, Lakewood, CO) system was used for collection in either autologous plasma or Isoplate (65% Isoplate, 35% plasma). Platelet concentrations were determined on an Advia® 2120i (Siemens, Malvern, PA) and adjusted to 250,000 platelets/μL with autologous PPP, unless indicated otherwise.

B. Microplate Clot Retraction Method.

Individual wells of a 96-well polystyrene microplate were coated with 150 μL of anti-adherence rinse solution (Stem Cell Technologies, Vancouver, Canada) and the microplate was centrifuged for 10 minutes at 1,300 xg. The anti-adherence coating solution was aspirated and the coated wells were washed once with phosphate buffered saline. After washing, one side of each coated well was scored with an 18 Gauge (Ga) needle. Five μL of 30 U/ml thrombin (Haematologic Technologies, East Junction, VT) were added to each coated and scored well to initiate platelet aggregation, clot formation, and subsequent clot retraction. PRP was supplemented with 6 mM $CaCl_2$ (Sigma, St. Louis, MO) before aliquoting 180 μL to wells that were adjacent to the thrombin-containing (reaction) wells. The transfer of PRP to adjacent (staging) wells allowed for simultaneous transfer of multiple samples to the reaction wells using a multichannel pipette. The microplate was then loaded into a Synergy™ Neo2 microplate reader, and 145 μL of re-calcified PRP were transferred from the staging well to the reaction well. The plate scan was immediately started after addition of PRP. The plate scan protocol consisted of: temperature=37° C., assay duration=30 minutes, read interval=5 seconds, kinetic absorbance wavelength=350 nm, well scan absorbance wavelength=350 nm. After the plate scan protocol was completed, the plate was discarded and the data were exported as text files.

C. Clot Retraction Agonists and Antagonists.

When indicated, the concentrations of platelets, CaCk, or thrombin were varied to identify the optimal assay conditions for clot retraction. Additionally, PRP was pre-treated with increasing concentrations of inhibitors to platelet integrin $\alpha_{IIb}\beta_3$ (Eptifibatide, Sigma, St. Louis, MO), platelet-fibrin interaction (RGDS, Cayman Chemical, Ann Arbor, MI), and Src-family kinase (PP2, Sigma). Vehicle controls were the solvent used for the respective compound. Each treatment was performed in at least duplicate technical replicates.

D. Light Transmission Aggregometry (LTA).

PRP platelet concentration was adjusted to 250,000 platelets/μL in autologous PPP. The optical density configuration of the Model 700 (Chrono-log, Havertown, PA) was used to evaluate platelet aggregation upon stimulation with ADP+collagen (10 μM+0.5 μg/mL) or Thrombin Receptor Activating Peptide 6 (TRAP-6, 10 μM), according to the manufacturer's recommendation. The maximum amplitude (MaxA), Slope, and Area Under Curve (AUC) parameters were exported as text files.

E. Parameterization of Microplate Clot Retraction Method.

Text files containing the optical density (O.D.) values were imported into R v4.0.5. Parameters of Rate of Clot Formation, Rate of Clot Retraction, Maximum O.D., Retraction Coefficient, Time to Maximum O.D., and Retraction Time were derived for each sample. Algorithms to extract parameters are described in Table 2, below.

TABLE 2

Precision and reference values for six parameters derived from the clot retraction time-series data.

| Parameter | Parameterization | Coefficient of Variation (n = 5) Minimum | Median | Mean | Maximum | Reference Intervals (n = 25) LL (CI) | UL (CI) |
|---|---|---|---|---|---|---|---|
| Rate (Clot Formation) | max{arr[f(s)]} where f(s) fits a linear model to the data using a sliding window procedure (k = 20) and extracts the slope coefficient. | 11.78 | 14.35 | 13.87 | 18.08 | 0.0018 (0.0011, 0.0024) | 0.0067 (0.0061, 0.0074) |
| Rate (Clot Retraction) | abs{min{arr[f(s)]}} where f(s) fits a linear model to the data using a sliding window procedure (k = 20) and extracts the slope coefficient. | 6.34 | 7.61 | 8.74 | 10.21 | 0.0016 (0.00018, 0.0030) | 0.012 (0.011, 0.014) |
| Maximum O.D. | max(Y). Depicted in FIG. 1b as the Y-value where the vertical red line and curve intersect. | 1.86 | 2.51 | 2.45 | 3.72 | 1.53 (1.41, 1.65) | 2.38 (2.24, 2.50) |
| Retraction Coefficient | [max(Y) − min($Y_i$)]/max(Y) where $Y_i$ occurs after max(Y). | 0.99 | 1.17 | 1.23 | 1.68 | 0.55 (0.49, 0.61) | 0.89 (0.84, 0.96) |
| Time to Max. O.D. | X-value at coordinate point (X, max(Y)). Depicted in FIG. 1b as the time-point where the vertical red line and x-axis intersect. | 3.04 | 4.69 | 4.66 | 6.52 | 410 (328, 475) | 962 (889, 1039) |
| Retraction Time | X-value for the first instance where $Y_i < Y_1$. $Y_1$ is the O.D. at 0 sec and $Y_i$ occurs after max(Y). Depicted in FIG. 1b as the time-point where the vertical blue line and x-axis intersect. | 2.43 | 3.92 | 3.66 | 6.46 | 604 (500, 690) | 1279 (1198, 1368) |

Figure 2:
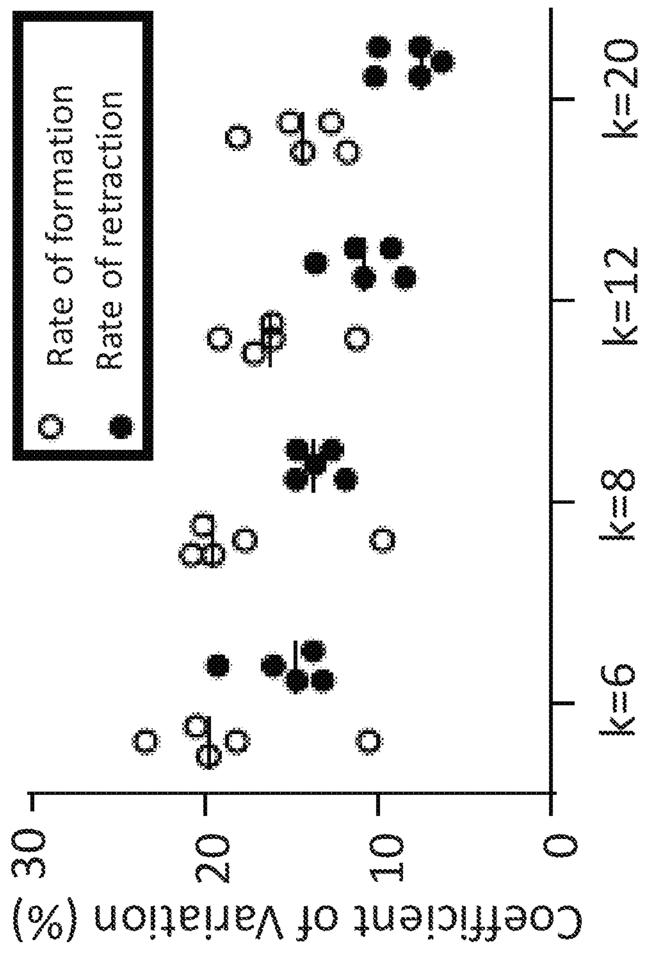
FIG. 2 shows the rates of clot formation and retraction, derived from time-series data of five donors using 6, 8, 12, or 20 consecutive data points (k).

Briefly, for Rates of Clot Formation and Retraction, a sliding window procedure was used to fit a linear model to a subset of 20 consecutive data points (k=20). The slope coefficient was extracted from each linear model and stored in an array. The Rates of Clot Formation and Retraction were defined as the maximum and minimum values, respectively, in the array. Initial experiments showed that k=20 gave the smallest coefficient of variation for both rate parameters. See FIG. 2, which shows rates of clot formation and retraction derived from time-series data of five donors using k sizes of 6, 8, 12, or 20. The data points represent donors and horizontal bars depicts medians. The Maximum and Minimum O.D. values were defined as the maximum and minimum readings, respectively. The Retraction Coefficient was defined as the difference between the Maximum and Minimum O.D. values, divided by the Maximum O.D. value. The Time to Maximum O.D. was defined as the time-point in which the Maximum O.D. value was observed. Retraction Time was defined as the time-point for the first instance where the O.D. value was less than or equal to the first data point (t=0 sec) after reaching Maximum O.D.

F. Reference Intervals Estimation and Statistical Analyses.

The dataset (n=25) consisted of samples from 10 female and 15 males, between the ages of 21 and 64. Each donor was represented only once in the dataset. Outliers, identified by a Box-Cox transformation algorithm, were excluded from reference interval calculations. After removing outliers, 95% reference intervals were calculated using a robust procedure. This procedure is reported to perform well with small sample sizes and provide intervals that more closely resemble the underlying distribution. Finally, 90% confidence intervals were calculated using a bootstrapping method. All computations were performed in R v4.0.5 implementing the referenceIntervals package.

Differences between groups were evaluated by linear mixed effects models (restricted maximum likelihood) with subject and treatment as a random and fixed effects, respectively. Analysis of apheresis platelets included an interaction for storage day and storage solution. When residuals diagnostic plots revealed deviation from normality or non-constant variance, the data were transformed (log 2, square-root, etc.) and revaluated. For multiple comparison testing, Dunnett's test was used to compare treatments to vehicle control, while Tukey's test was used for all pair-wise comparisons. Due to censoring, Retraction Time data were analyzed using the logrank test. All statistical computations were performed in R v4.0.5 implementing the Ime4, multcomp, and survival packages. *p<0.05, p<0.01, *p<0.001. Data were plotted with GraphPad Prism v9.2.0.

G. Results.

Thrombin was used to initiate the assay reaction (clot formation and platelet activation). However, agonist-induced calcium flux is known to impact platelet function and variable platelet activation may affect the method's precision. To optimize the method's repeatability and reproducibility, the assay conditions were varied for platelet (n=6), CaCk (n=5), and thrombin (n=5) concentrations.

Figure 3:
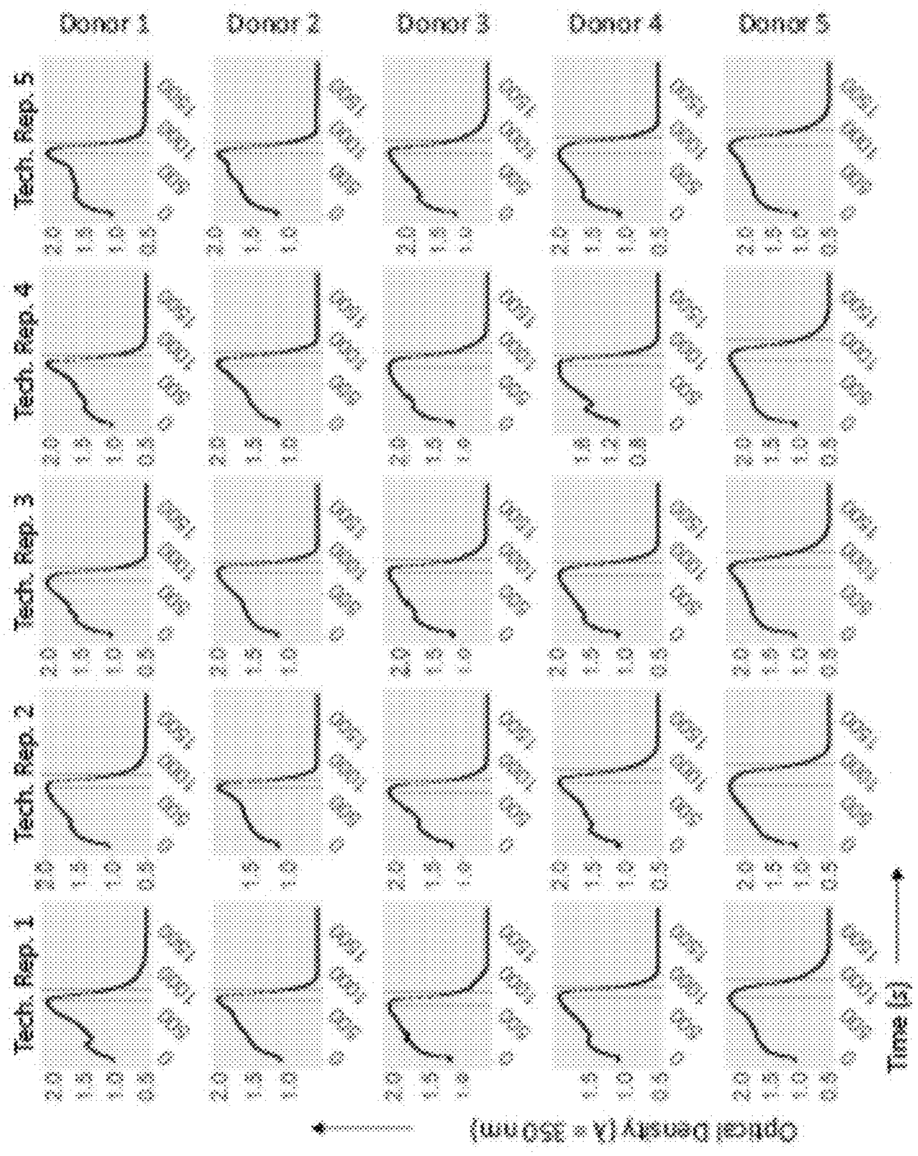
FIG. 3 is a series of plots showing the repeatability and reproducibility of the inventive microplate clot retraction method.

The assay was performed on five different days on samples from five different donors. Each day, the method was performed with five technical replicates. Solid line and ribbon depict the mean and 95% confidence interval of five technical replicates. Plots of individual technical replicates are shown in FIG. 3. The leftmost panel: red numbers (1-5) correspond to the phase of clot retraction described in the text.

Figure 4:
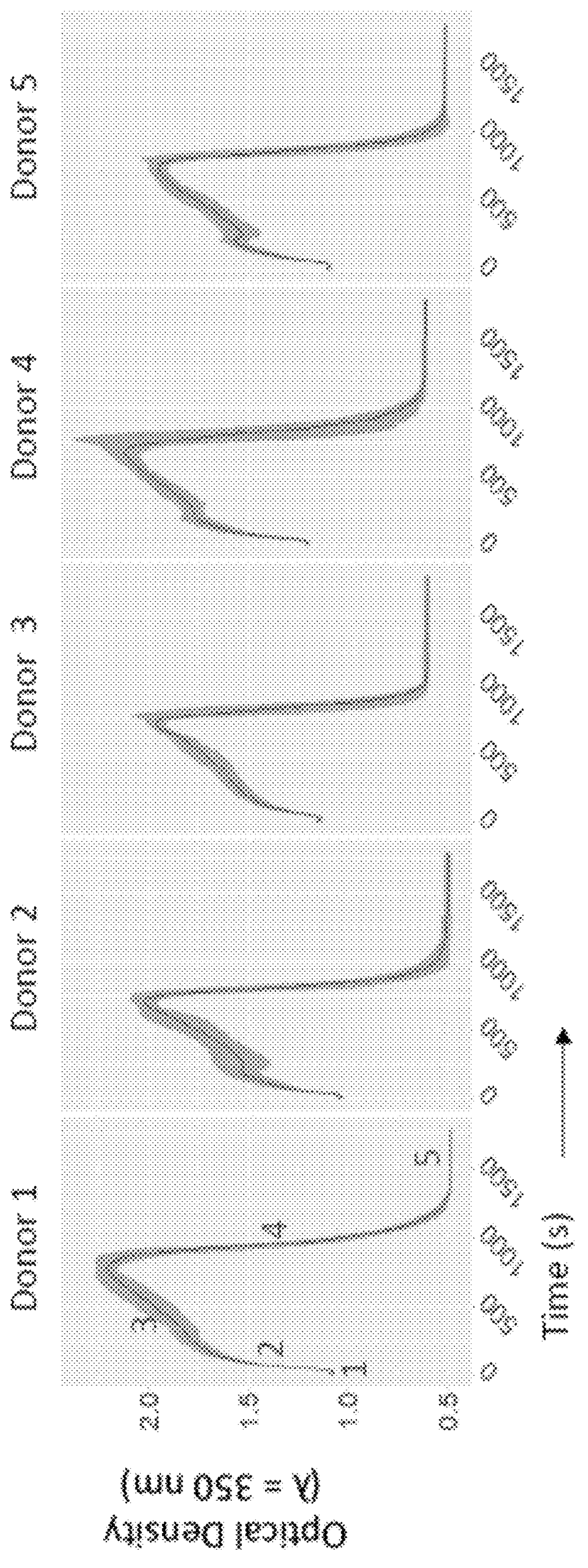
FIG. 4 presents results for an assay performed on five different days on samples from five different donors.
Figure 5C:
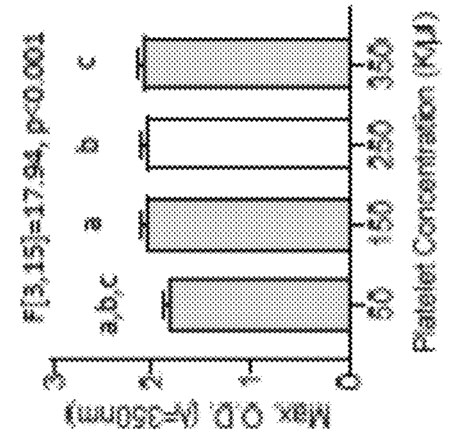
FIG. 5A through FIG. 5R are barplots of six parameters that were extracted from the time-series data showing the effect of platelet (FIG. 5A through FIG. 5F), thrombin (FIG. 5G through FIG. 5L), and $CaCl_2$) (FIG. 5M through FIG. 5R) concentration on clot retraction.
Figure 5B:
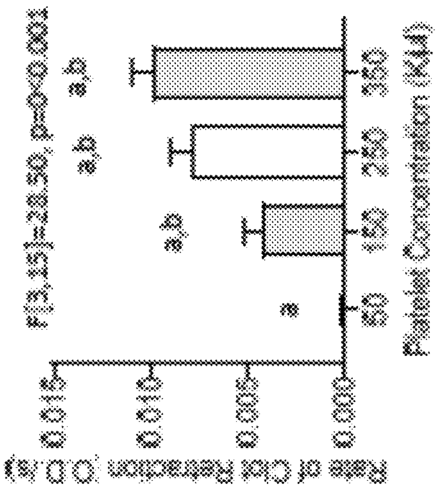
Figure 5A:
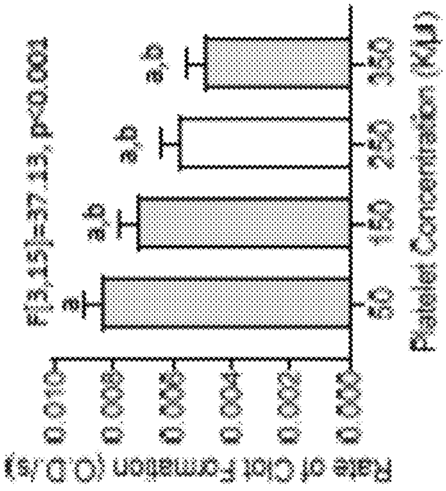
Figure 5D:
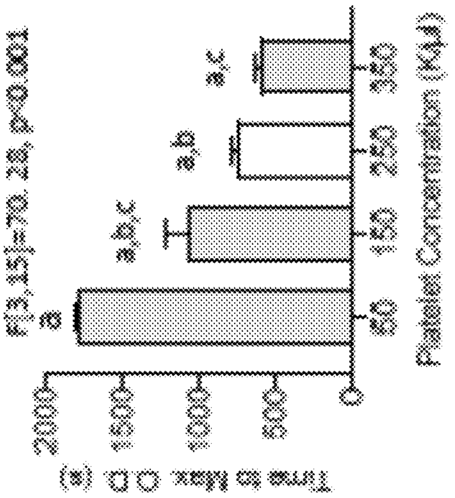
Figure 5E:
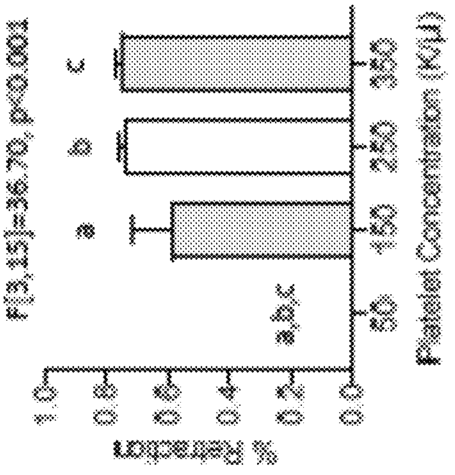
Figure 5F:
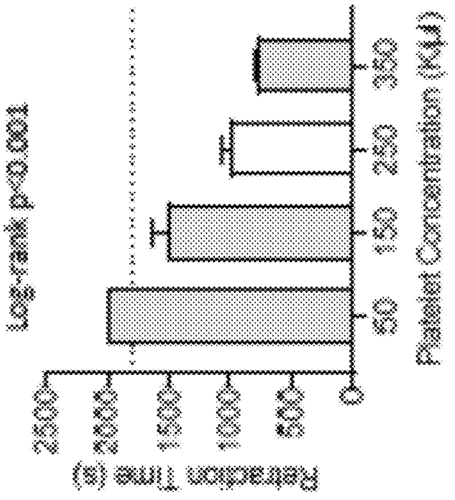
Figure 5G:
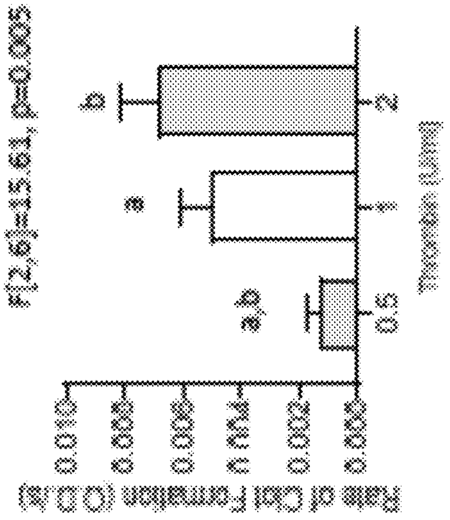
Figure 5H:
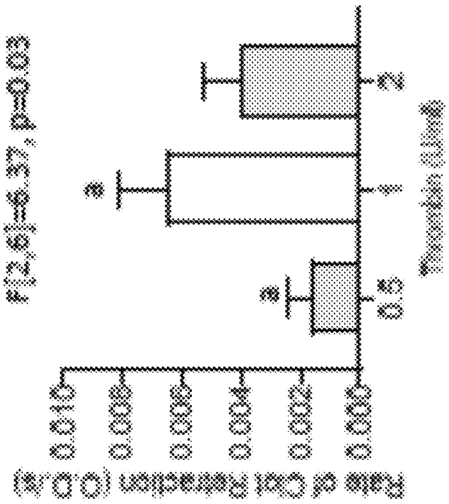
Figure 5I:
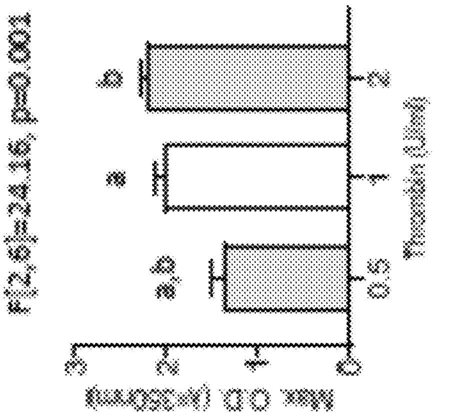
Figure 5J:
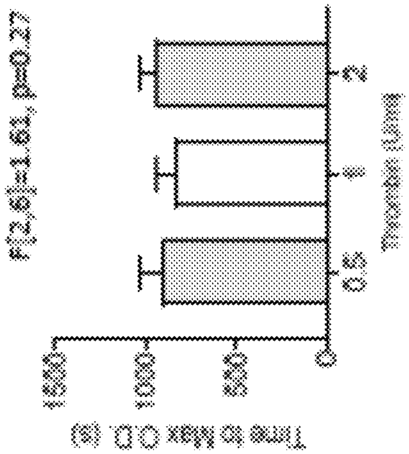
Figure 5K:
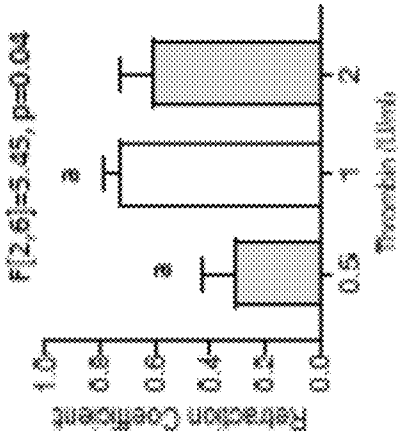
Figure 5L:
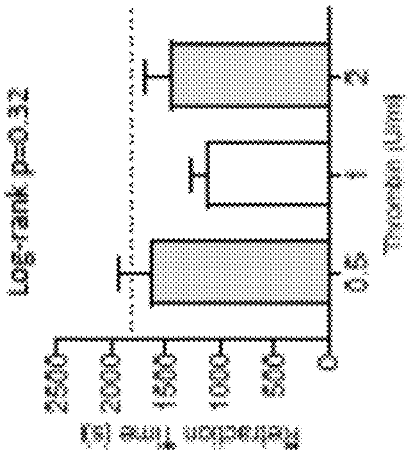
Figure 5M:
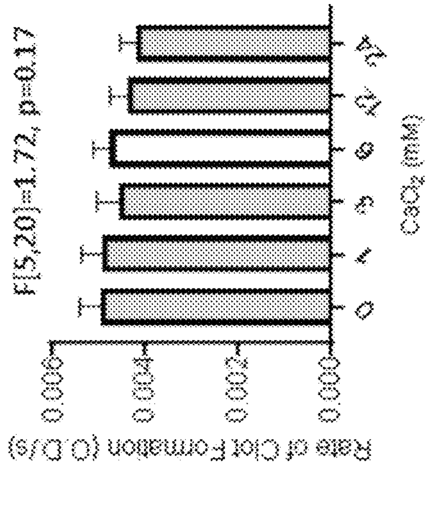
Figure 5N:
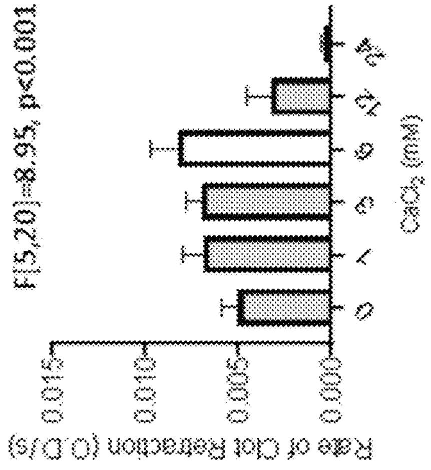
Figure 5O:
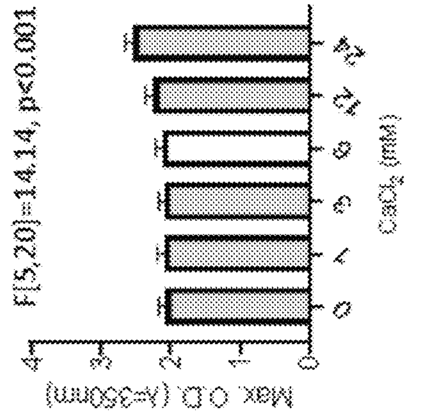
Figure 5R:
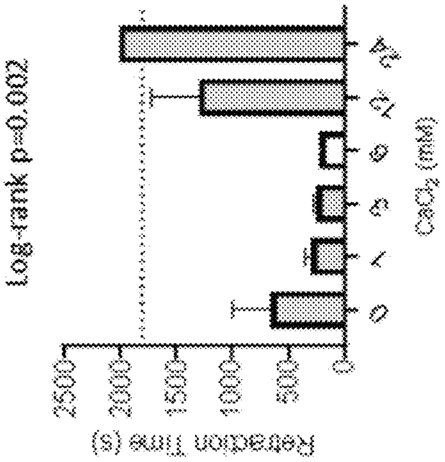
Figure 5Q:
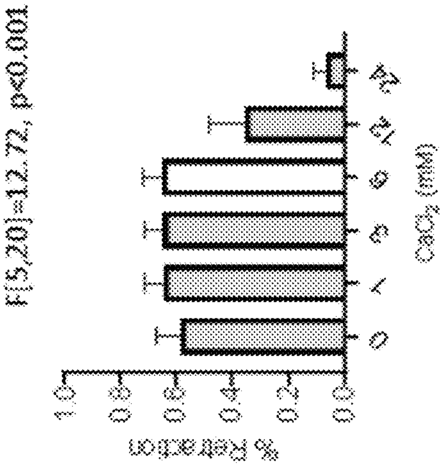
Figure 5P:
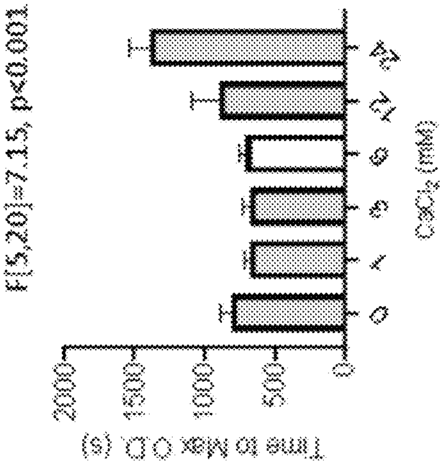

Upon initiation of the reaction, the O.D. kinetics had a very short lag phase (phase 1), a primary clotting phase (phase 2), a clot densification phase (phase 3), a retraction phase (phase 4), and a resolved phase (phase 5). See FIG. 4, where the leftmost panel numbers indicate phase). To objectively evaluate the O.D. readings, an algorithm was developed to extract the following six parameters from the time-series data: Maximum O.D., Time to Maximum O.D., Rate of Clot Formation, Rate of Clot Retraction, Retraction Time, and Retraction Coefficient. Table 2 describes the function used to extract each of the above parameters, along with each parameter's repeatability (coefficient of variation) and reference intervals.

Platelet and thrombin concentrations significantly affected the method's results in a concentration dependent manner (see FIG. 5A through 5L). Notably, 250 K/μL platelets and 1 U/mL thrombin were the lowest concentrations which had small variance, reproducible results, and consistent clot retraction within the method's runtime. These conditions were chosen for all subsequent experiments. Significant differences among $CaCl_2$) concentrations were found with the highest levels resulting in clot formation, but failure in clot retraction (see FIG. 5M through 5R). No differences were found across a range of 0 to 6 mM CaCk; thus, 6 mM $CaCl_2$ was chosen for all subsequent experiments. For FIG. 5, which are barplots of six parameters that were extracted from the time-series data showing the effect of (b) platelet, (c) thrombin, and (d) $CaCl_2$) concentration on clot retraction, the bars and error bars depict the mean and SEM, respectively. Differences among the treatment concentrations were analyzed by linear mixed effects models with Tukey's post-hoc tests to determine pairwise differences. Unfilled bars represent the condition used for subsequent experiments. Due to censoring, Retraction Time data were analyzed with a logrank test. Horizontal dashed line shows the assay end-point; data points above the line are censored. Shared letters above bars indicate significant ($p<0.05$) pairwise differences.

The method's precision was evaluated on five individual donors, each with five technical replicates. The method was performed for each donor on separate days. See FIG. 3. All five donors yielded similar O.D. kinetics that are characteristic for this method (see FIG. 2 and FIG. 3). The parameter with the greatest variability was rate of clot formation with a median coefficient of variation (CV) of 14.35% (Table 2). All other parameters had median CV values of <8%, indicating that the inventive microplate clot retraction assay method has relatively high repeatability and reproducibility.

Figure 6A:
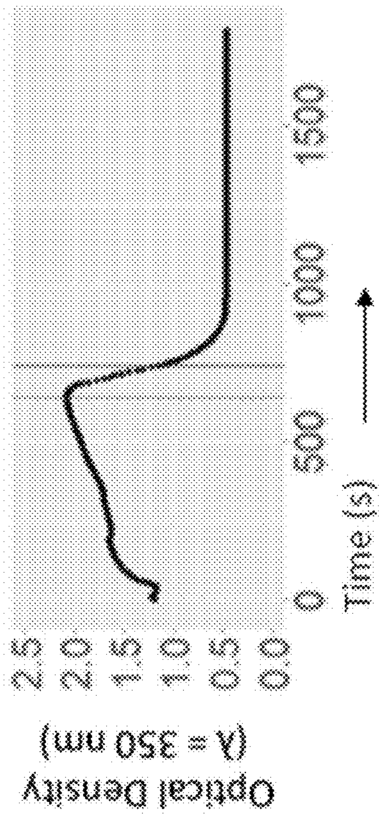
FIG. 6A and FIG. 6B show representative examples of typical (6A) and delayed (FIG. 6B) clot retraction in healthy donor samples.
Figure 6B:
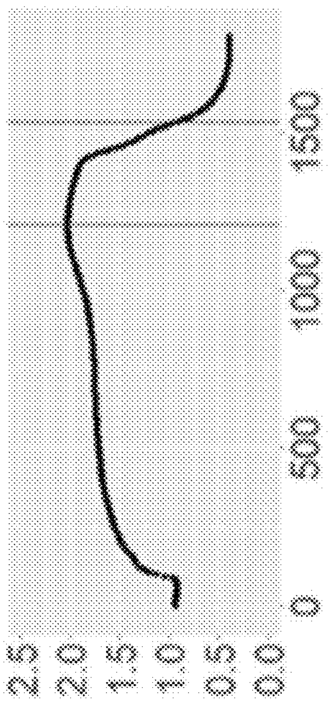
Figures 7A, 7B, 7C, 7D, 7E, 7F:
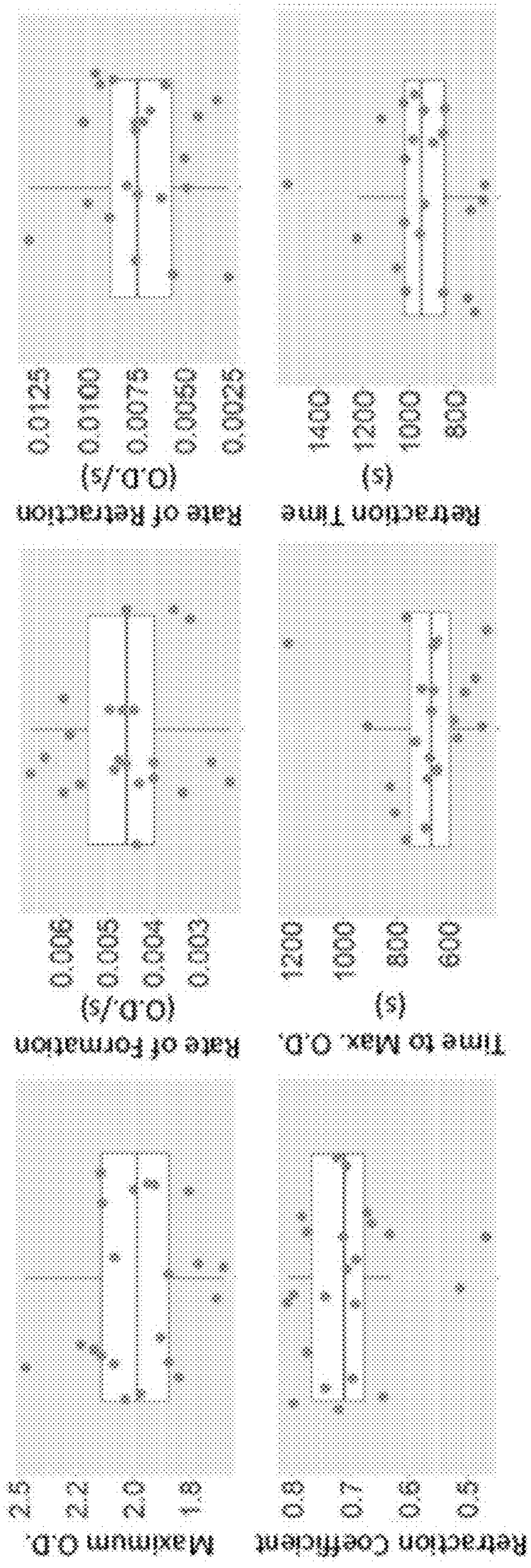
FIG. 7A through FIG. 7F show the distribution of six parameters derived from time-series data of healthy donor samples (n=25).

Reproducibility was shown to be consistent among the pool of healthy donors (n=25) and all parameters demonstrated a fairly Gaussian distribution with little skewness. See FIG. 7. Notably, the healthy donor pool had few outliers present (i.e., three outliers for Time to Maximum O.D. and two outliers for Retraction Time). See FIG. 6 and FIG. 7. FIG. 6A and FIG. 6B present a representative example of typical (A) and delayed (B) clot retraction in healthy donor samples. Vertical red line shows the Time to Maximum O.D. parameter value. Vertical blue line shows the Retraction Time parameter value. FIG. 7 provides the distribution of six parameters derived from time-series data of healthy donor samples (n=25). Boxplots show the median along with the first and third quartiles. Whiskers depict the standard error and data points represent an individual sample. These data suggest that clot retraction may exhibit individual differences among an otherwise healthy population. Based on the normal donor data, we computed preliminary reference intervals for each parameter (Table 2). These data demonstrate the robustness and Precision of the method.

Example 3. Effect of Fibrin (Ogen) Binding and Outside-In Signaling on Clot Retraction Platelet integrin $\alpha_{IIb}\beta_3$ provide important signals for irreversible platelet activation and subsequent contraction. We used increasing concentrations of Eptifibatide and Arg-Gly-Asp-Ser (RGDS) tetrapeptide to inhibit fibrin (ogen)-platelet interaction, and PP2 to inhibit intracellular kinase signaling. At the highest levels of inhibition, the clot densification phase (phase 3) was absent or greatly diminished from the reaction kinetic curve. See FIG. 8A and FIG. 9A, which provide data on assays of platelets pre-treated with Eptifibatide or PP2, and FIG. 10A).

Figure 8A:
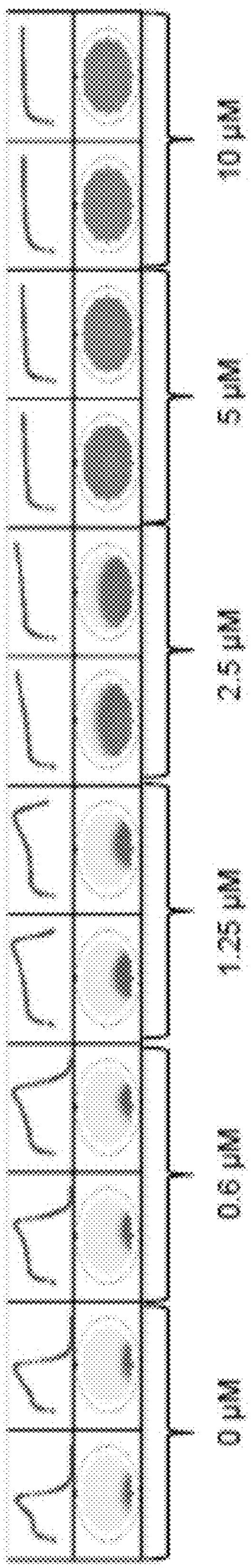
FIG. 8A through FIG. 8G show results of an assay performed using platelets pre-treated with Eptifibatide at the indicated concentrations (n=5).
Figure 8B:
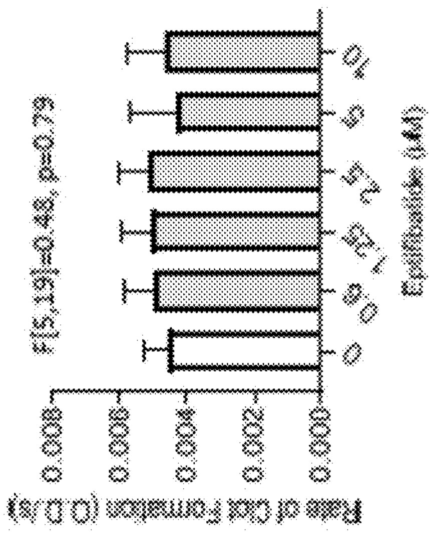
Figure 8C:
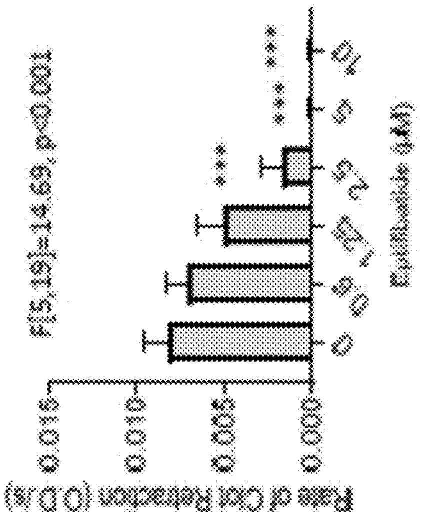
Figure 8D:
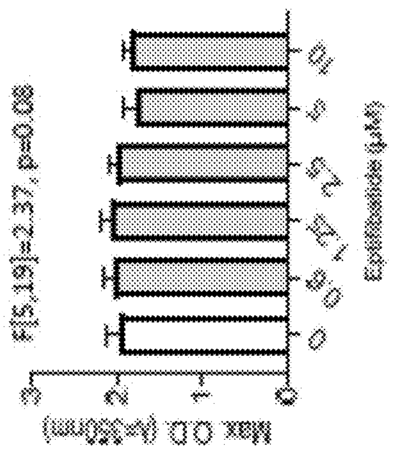
Figure 8G:
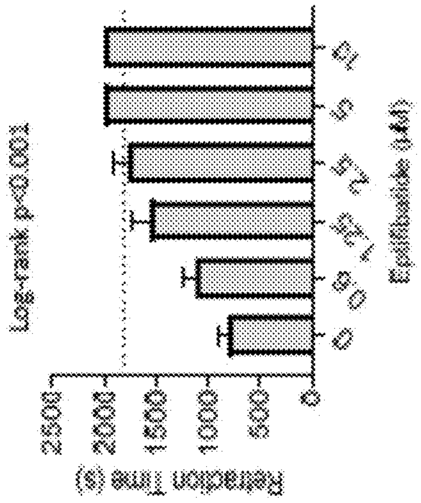
Figure 8F:
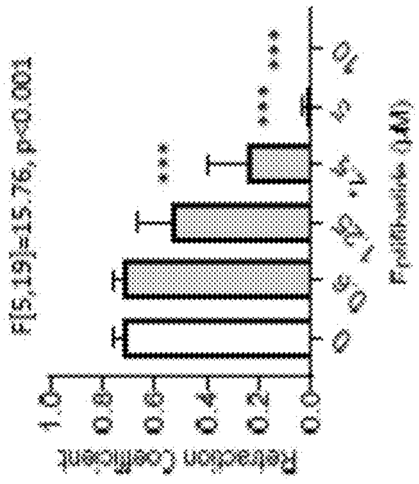
Figure 8E:
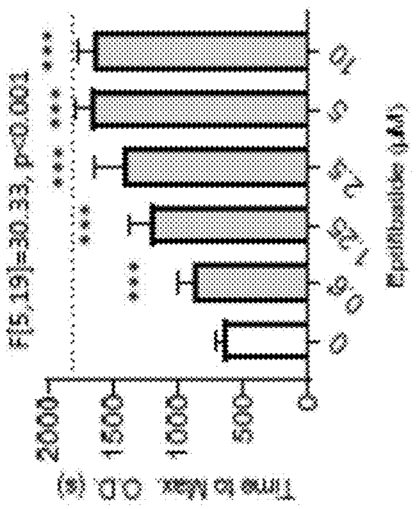
Figure 9A:
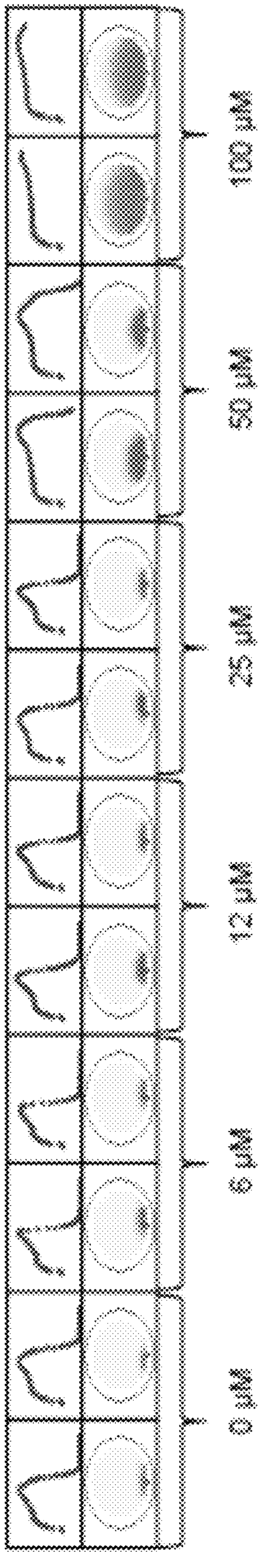
FIG. 9A through FIG. 9G show results of an assay performed using platelets pre-treated with PP2 at the indicated concentrations (n=5).
Figure 9D:
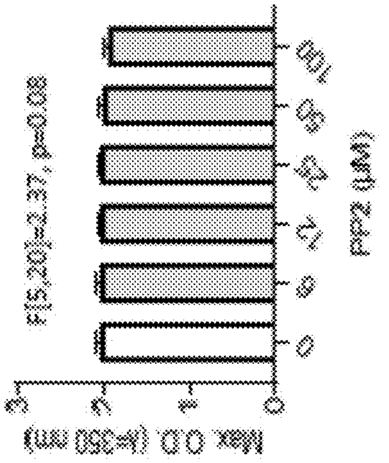
Figure 9C:
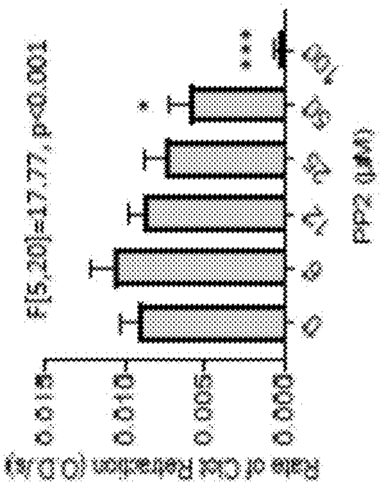
Figure 9B:
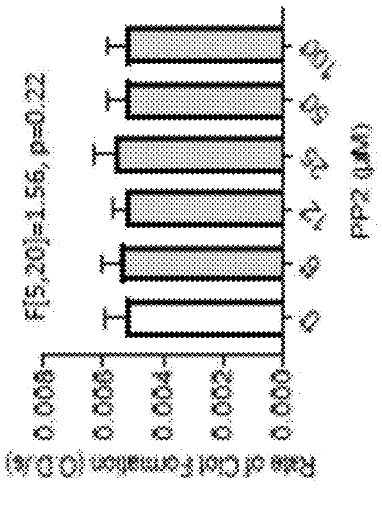
Figure 9E:
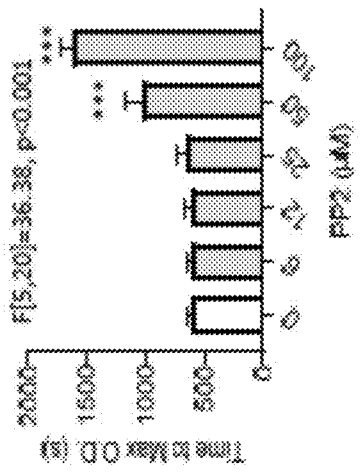
Figure 9F:
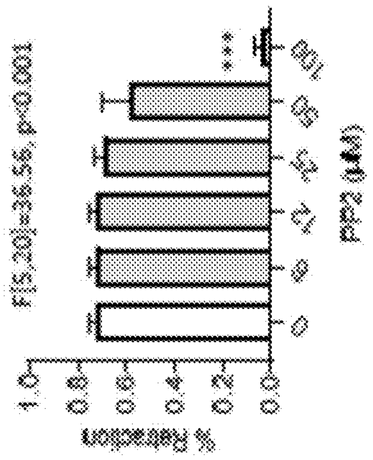
Figure 9G:
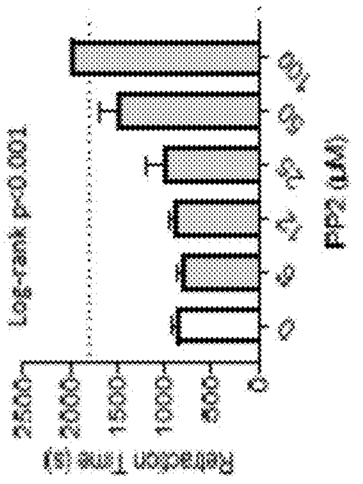
Figure 10A:
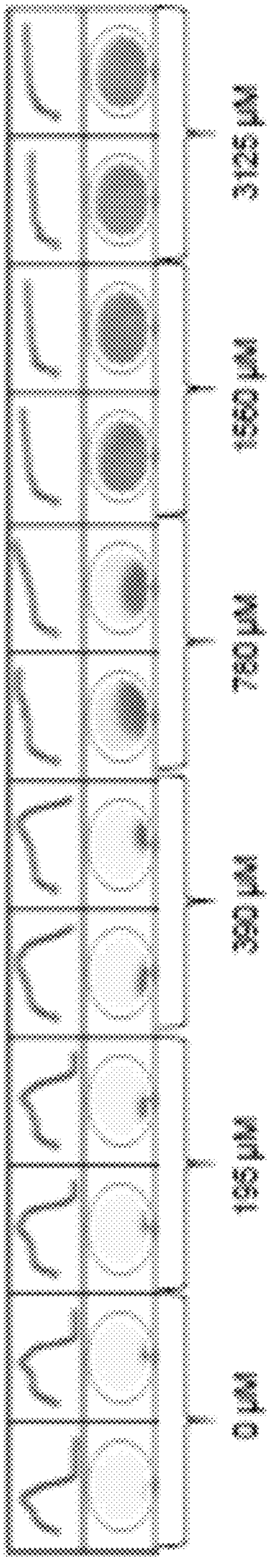
FIG. 10A is a representative time-series O.D. values (red traces) and end-point well scan (blue heatmap) which shows the size and position of the clot 30 min after initiating the reaction.
Figure 10D:
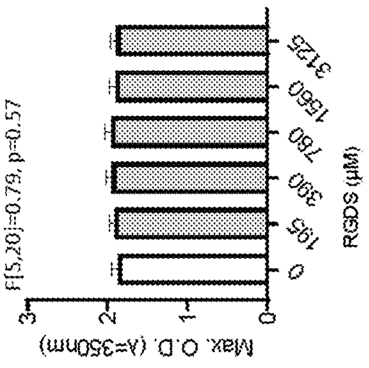
FIG. 10B through FIG. 10G are barplots of six parameters that were extracted from the time-series data.
Figure 10C:
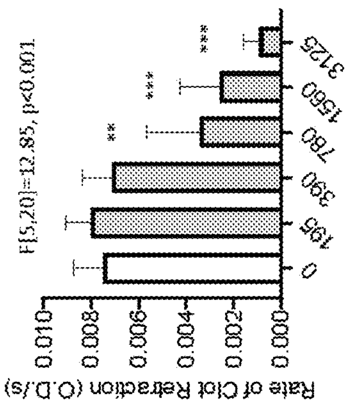
Figure 10B:
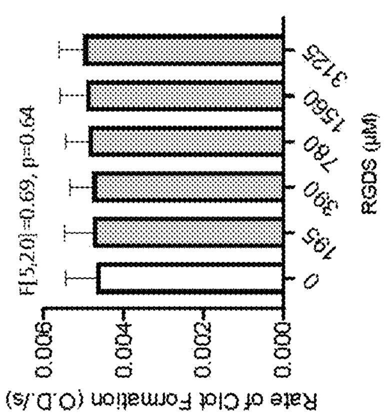
Figure 10E:
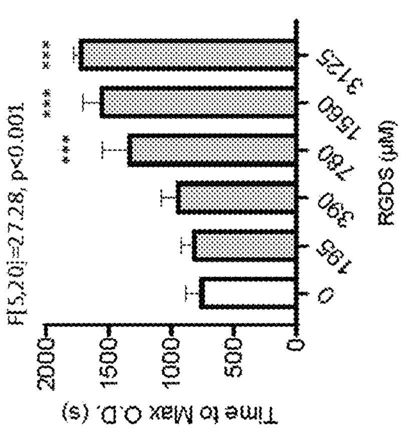
Figure 10F:
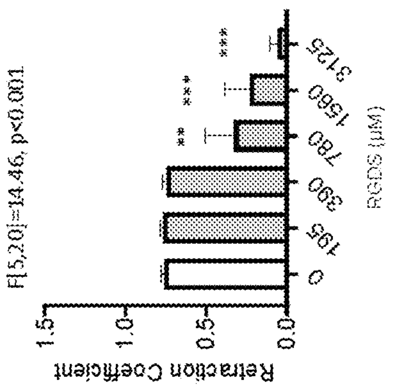
Figure 10G:
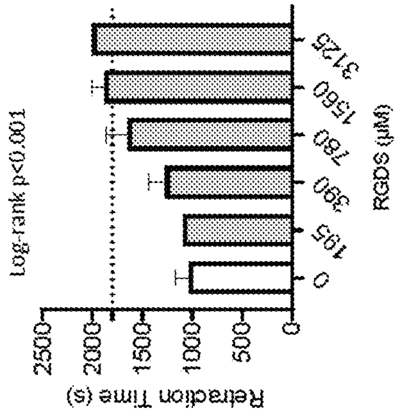
Figure 11A:
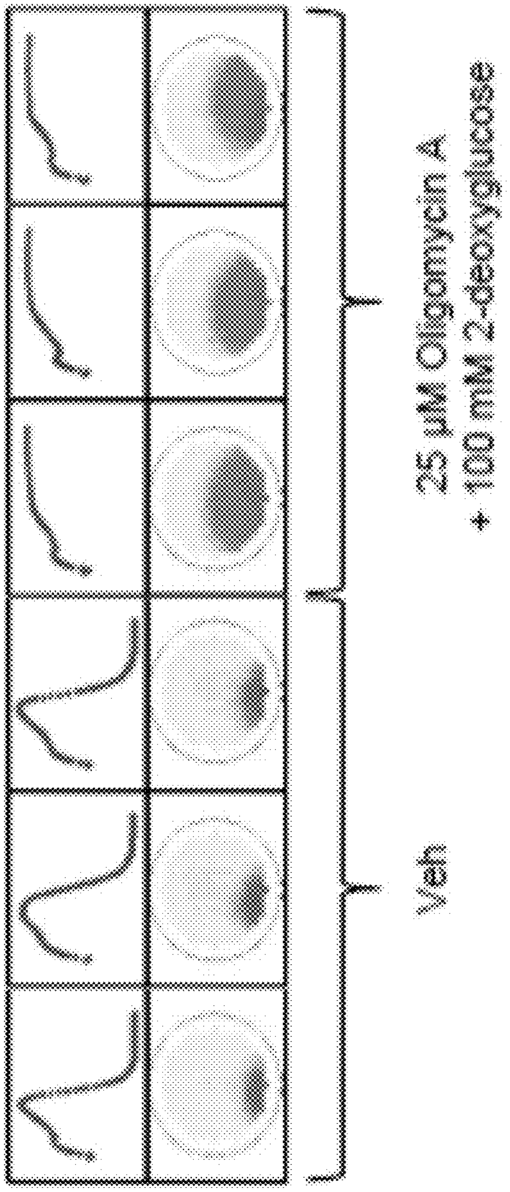
FIG. 11A through FIG. 11G show results of an assay performed using platelets pre-treated with an inhibitory cocktail of oligomycin A (25 μM) and 2-deoxyglucose (100 mM) (n=4).
Figure 11D:
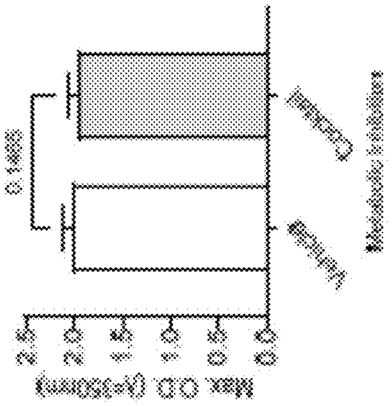
Figure 11C:
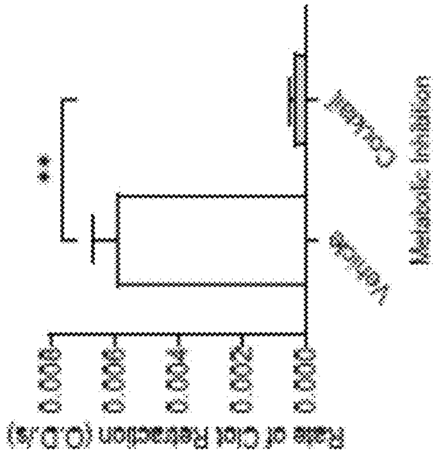
Figure 11B:
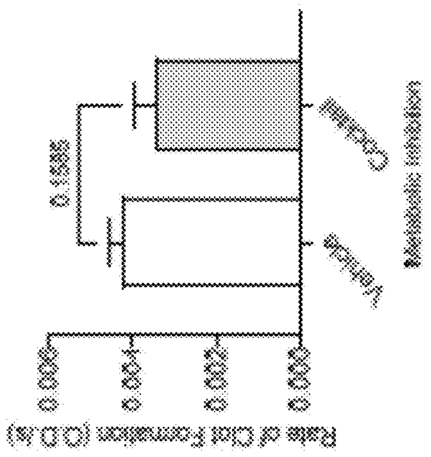
Figure 11E:
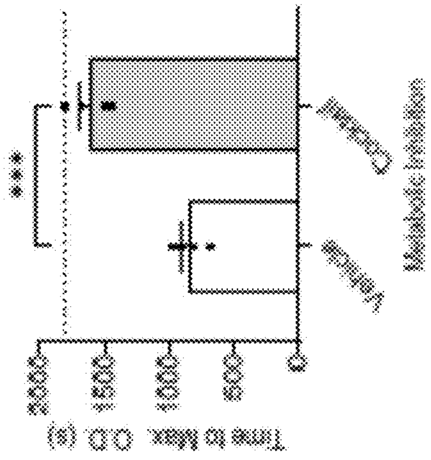
Figure 11F:
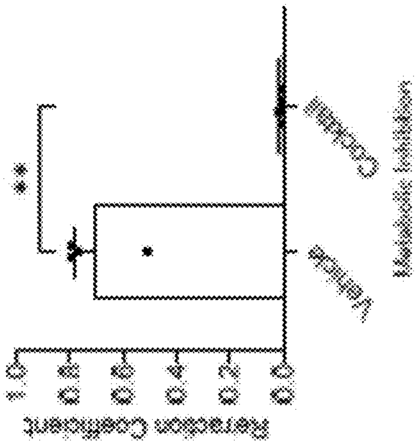
Figure 11G:
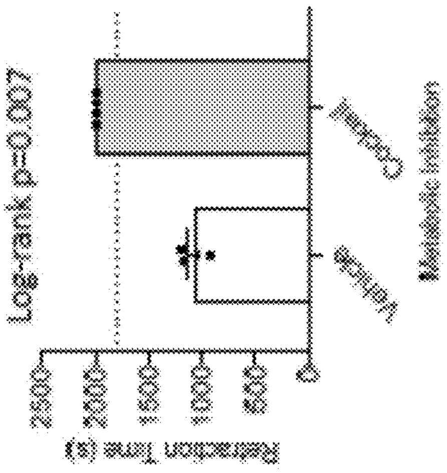
Figure 12A:
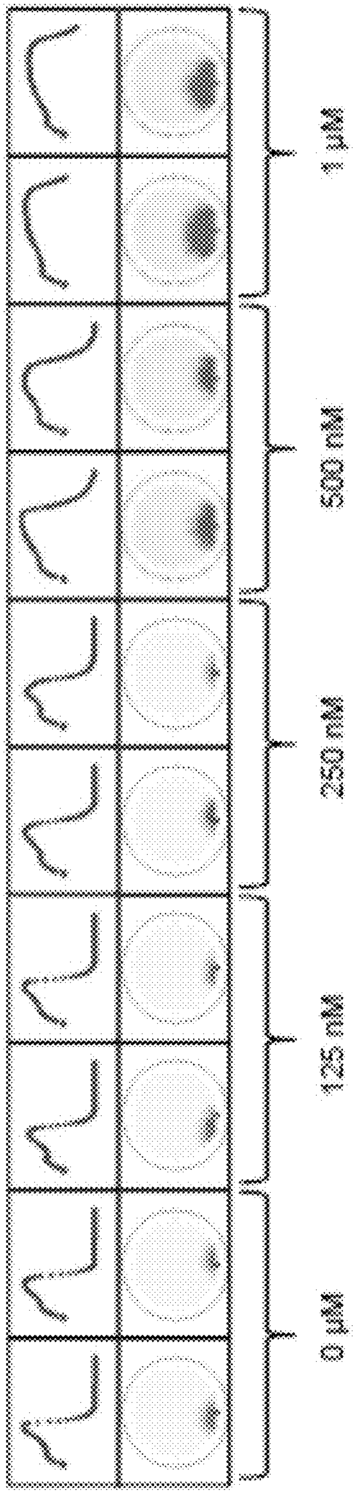
FIG. 12A through FIG. 12G show results of an assay performed using platelets pre-treated with cytochalasin D at the indicated concentrations (n=5).
Figure 12B:
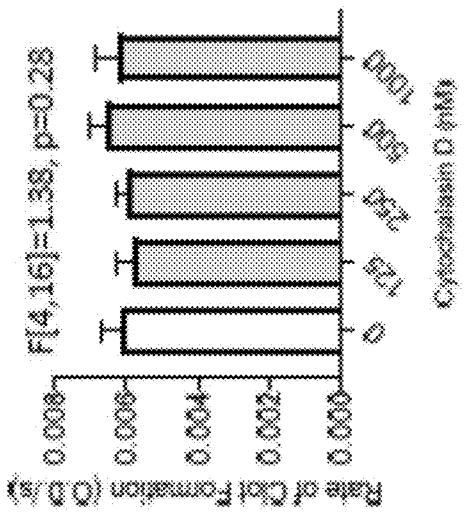
Figure 12C:
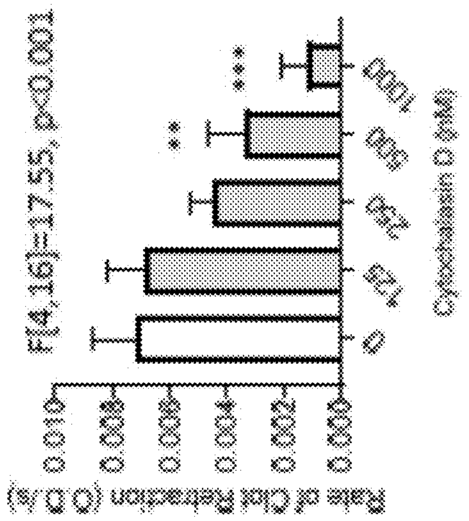
Figure 12D:
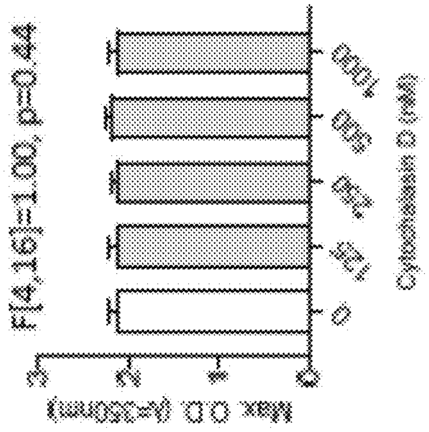
Figure 12E:
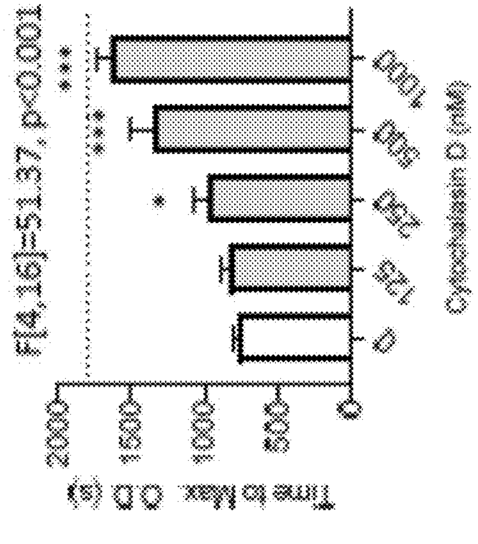
Figure 12F:
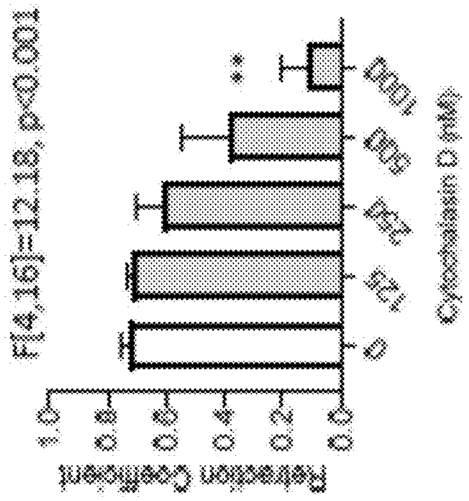
Figure 12G:
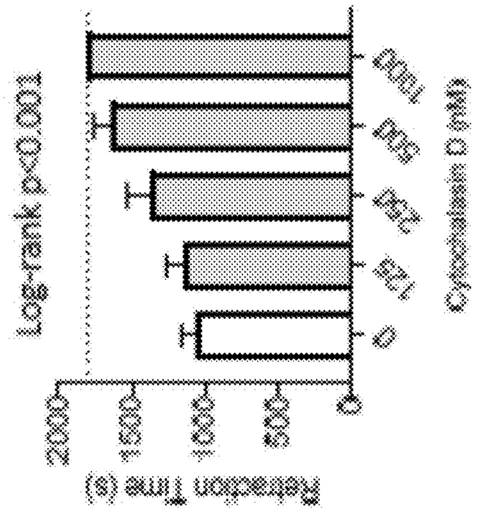

In FIG. 8A through FIG. 8G, the method was performed using platelets pre-treated with Eptifibatide at the indicated concentrations (n=5); in FIG. 9A through FIG. 9G, the method was performed using platelets pre-treated with PP2 at the indicated concentrations (n=5). FIG. 8A and FIG. 9A show representative time-series O.D. values (red traces) and end-point well scan (blue heatmap) which shows the position and size of the clot 30 min after initiating the reaction. FIG. 8B through 8G and FIG. 9B through 9G are barplots of six parameters that were extracted from the time-series data. Bars and error bars depict the mean and SEM, respectively. Differences among the treatment concentrations were analyzed by linear mixed effects models with Dunnett's post-hoc tests to determine differences compared to vehicle (unfilled bars). Due to censoring, Retraction Time data were analyzed with a logrank test. Horizontal dashed line shows the assay end-point; data points above the line are censored. *: $p<0.05$, : $p<0.01$, *: $p<0.001$. The data show that impaired fibrin (ogen) engagement and outside-in signaling is identified by the microplate clot retraction method.

All tested compounds showed dose-dependent inhibition of Rate of Retraction and Retraction Coefficient, and a delay in Retraction Time and Time to Maximum O.D ($p<0.001$). None of the tested inhibitors at any concentration significantly affected Rate of Clot Formation and Maximum O.D.

For FIG. 10, the method was performed using platelets pre-treated with RGDS tetrapeptide at the indicated concentrations (n=5). FIG. 10A presents a representative time-series O.D. values (red traces) and end-point well scan (blue heatmap) which shows the size and position of the clot 30 min after initiating the reaction. FIG. 10B through FIG. 10G is a set of barplot of six parameters that were extracted from the time-series data. Bars and error bars depict the mean and SEM, respectively. Differences among the treatment concentrations were analyzed by linear mixed effects models with Dunnett's post-hoc tests to determine differences compared to vehicle (unfilled bars). Due to censoring, Retraction Time data were analyzed with a logrank test. Horizontal dashed line shows the assay end-point; data points above the line are censored. *: $p<0.05$, : $p<0.01$, *: $p<0.001$.

Example 4. Effect of Platelet Bioenergetics and Actin Inhibition on the Clot Retraction Clot retraction is an energy-intensive process requiring extensive platelet cytoskeletal rearrangement. To evaluate the impact of platelet bioenergetics on clot retraction, we pretreated platelets in PRP with a cocktail of metabolic inhibitors that target glycolysis (100 mM 2-dexoyglucose) and ATP synthase (25 μM oligomycin A). There was a significant difference between vehicle and cocktail treated platelets for all parameters ($p<0.01$) except for Rate of Clot Formation and Maximum O.D. See FIG. 11A through FIG. 11G).

In experiments with impaired actin polymerization (cytochalasin D pretreatment), there were significant differences among treatment levels for all parameters ($p<0.001$) except for Rate of Clot Formation and Maximum O.D. See FIG. 12A through FIG. 12G). The differences among conditions followed the dosing level, with the greatest departure from vehicle treatment found at the highest cytochalasin D concentrations.

In FIG. 11, the method was performed using platelets pre-treated with an inhibitory cocktail of oligomycin A (25 μM) and 2-deoxyglucose (100 mM) (n=4); in FIG. 12, the method was performed using platelets pre-treated with cytochalasin D at the indicated concentrations (n=5). FIG. 11A and FIG. 12A provide representative time-series O.D. values (red traces) and end-point well scan (blue heatmap) which shows the size and position of the clot 30 min after initiating the reaction. FIG. 11B through FIG. 11G and FIG. 12B through FIG. 12G are barplots of six parameters that were extracted from the time-series data. Bars and error bars depict the mean and SEM, respectively. Paired t-tests were used to compare differences between vehicle and cocktail for metabolic inhibitors. Differences among cytochalasin D treatments were analyzed by linear mixed effects models with Dunnett's post-hoc tests to determine differences compared to vehicle (unfilled bars). Due to censoring, retraction time data were analyzed with a logrank test. Horizontal dashed line shows the assay end-point; data points above the line are censored. *: $p<0.05$, : $p<0.01$, *: $p<0.001$. The data here show that impaired metabolic activity and actin polymerization is identified by the microplate clot retraction method.

Figure 13:
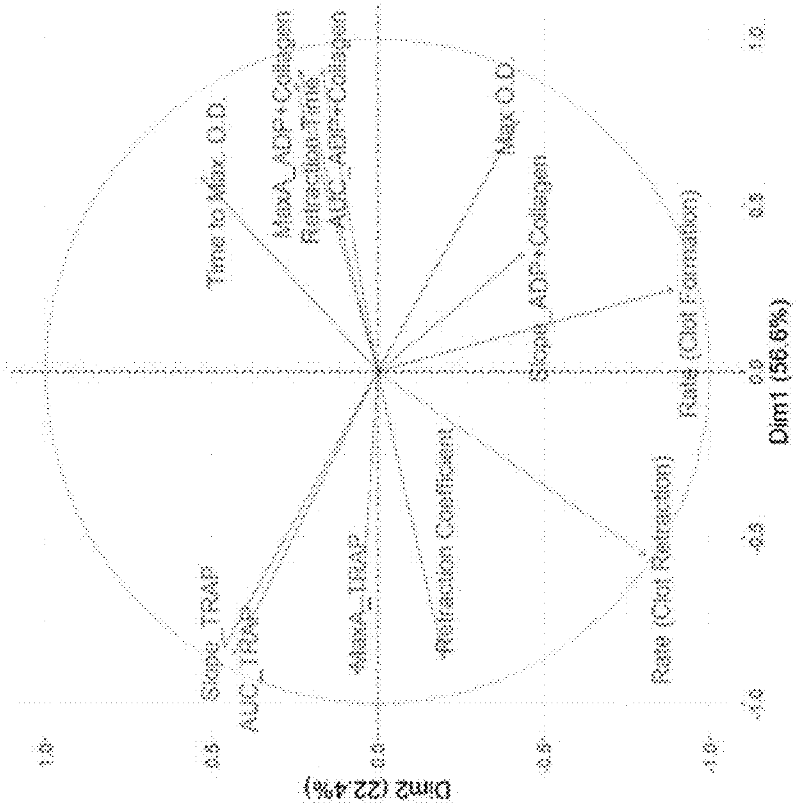
FIG. 13 is a principal component analysis variable plot showing the approximate relationship of microplate clot retraction (orange), LTA with TRAP agonist (green), and LTA with ADP+Collagen (purple) parameters.
Figure 14A:
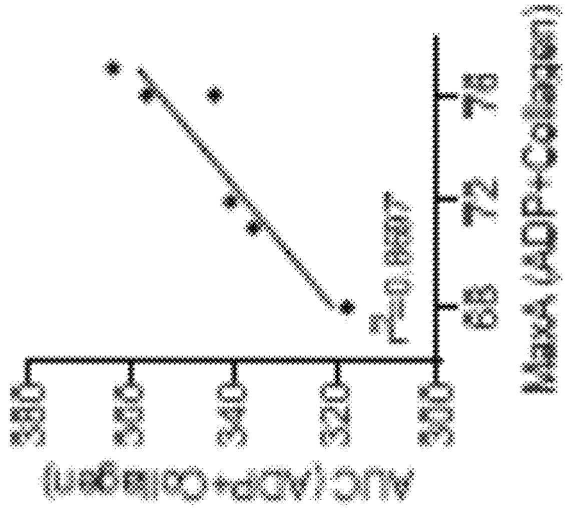
FIG. 14A and FIG. 14B are graphs showing strong correlation of different parameters using the same agonist.
Figure 14B:
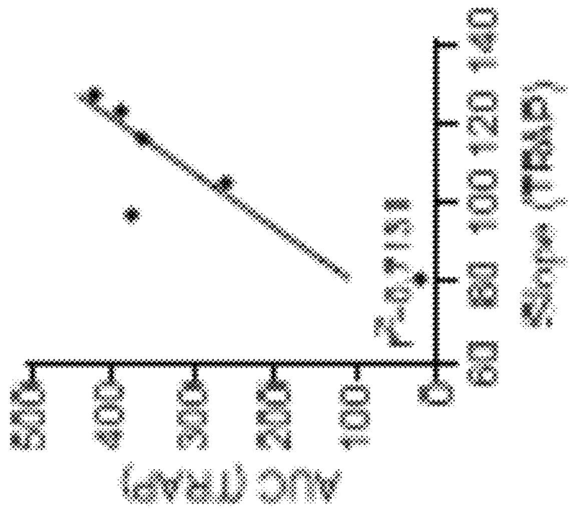
Figure 14A:
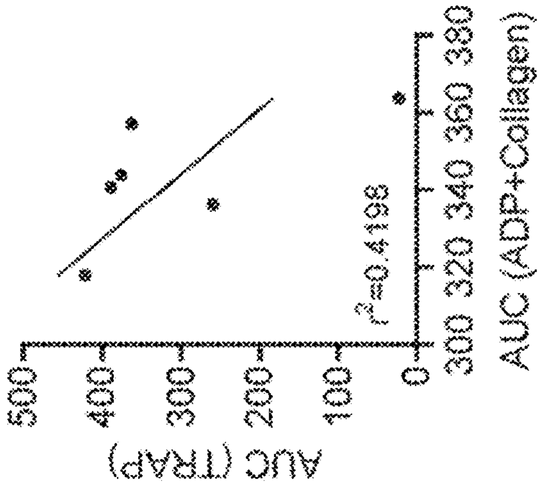
Figure 14B:
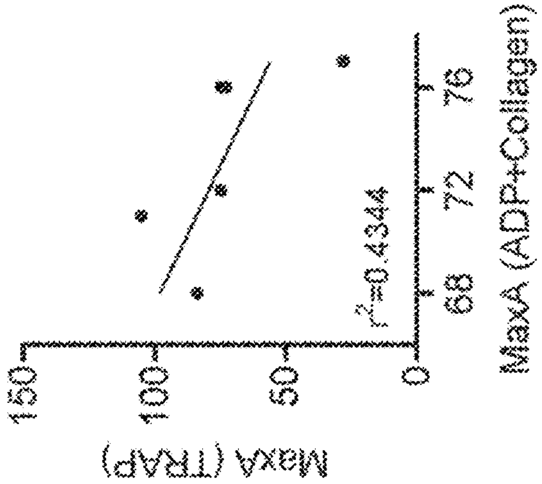
Figure 14C:
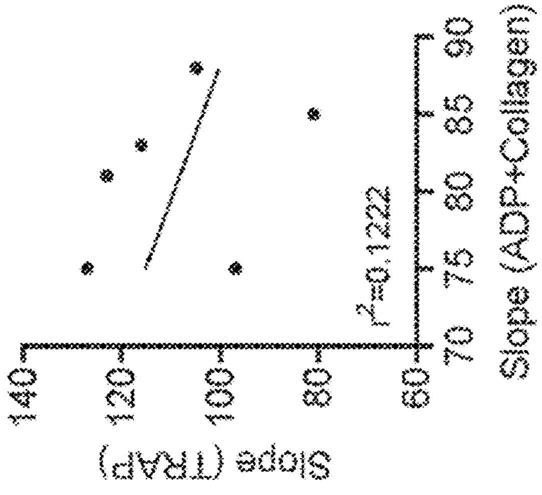
Figure 15A:
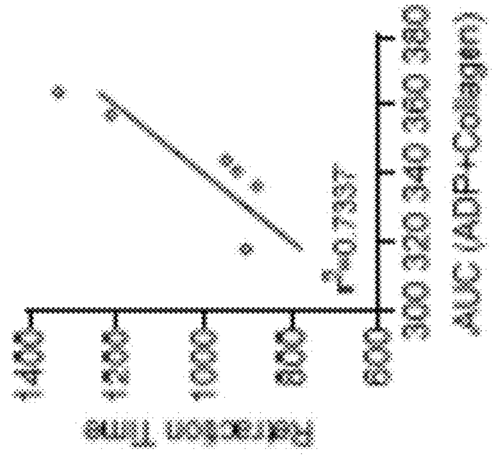
FIG. 15A, FIG. 15B, FIG. 15C, FIG. 15D and FIG. 15E present linear regression analysis of microplate clot retraction parameters that were significantly correlated with LTA ($p<0.05$).
Figure 15B:
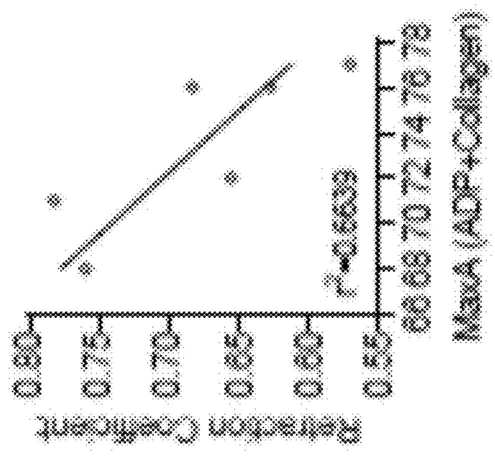
Figure 15C:
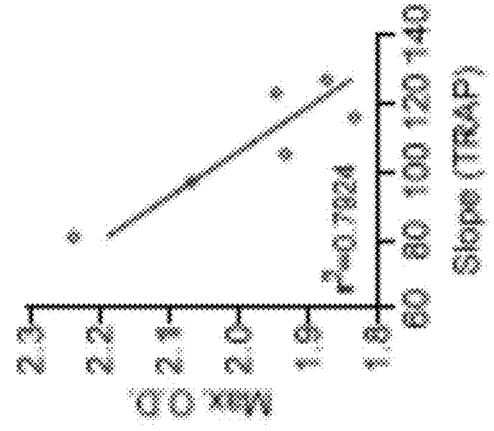
Figure 15E:
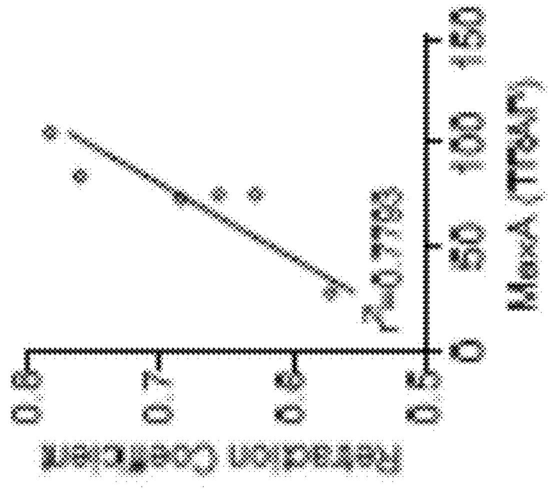
Figure 15D:
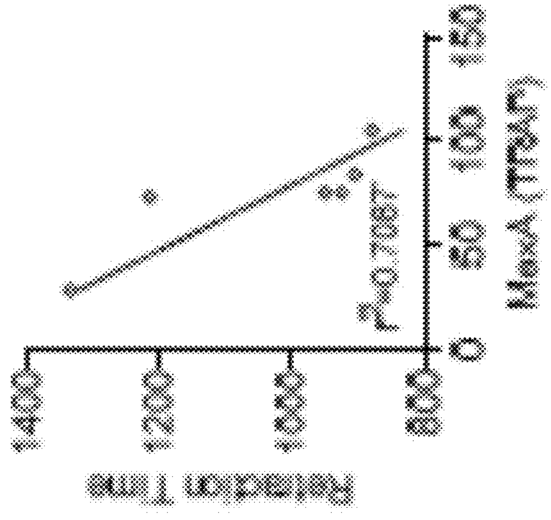
Figure 16A:
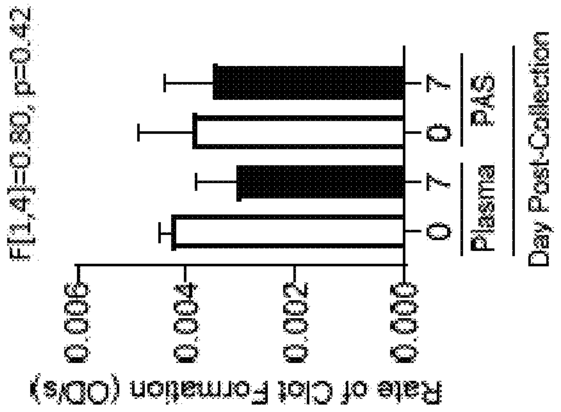
FIG. 16A, FIG. 16B, and FIG. 16C show the effects of apheresis platelets storage on microplate clot retraction parameters.
Figure 16B:
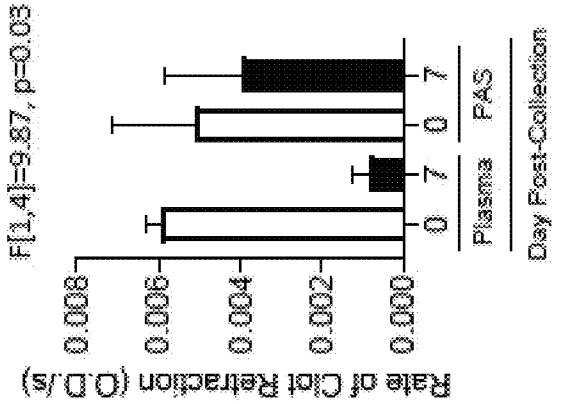
Figure 16C:
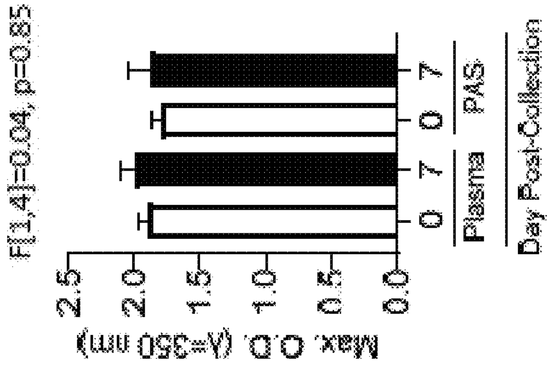
Figure 16F:
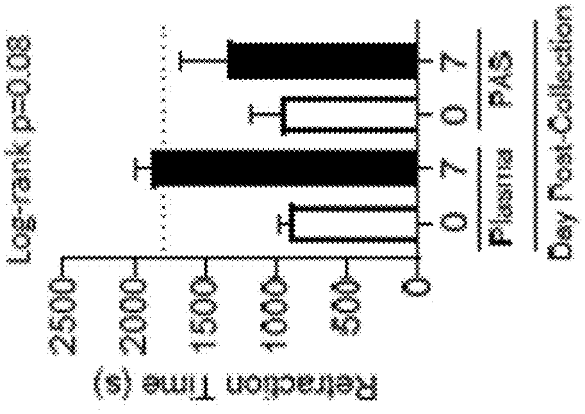
Figure 16E:
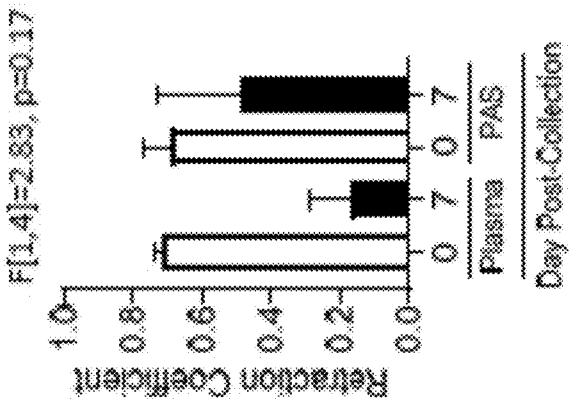
Figure 16D:
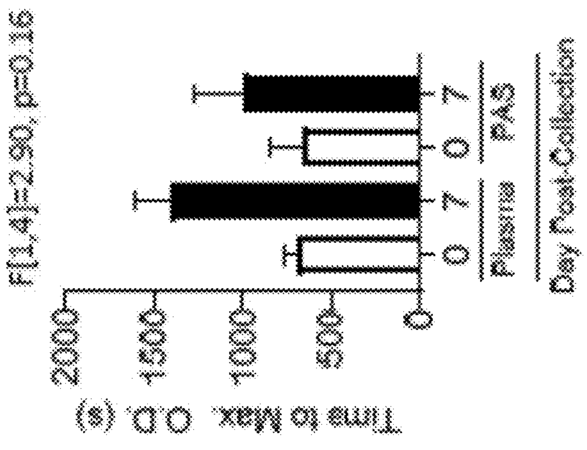

Example 5. Comparison of Microplate Clot Retraction and Light Transmission Aggregometry Light transmission aggregometry (LTA) is widely accepted as a gold standard for evaluating platelet function. To benchmark the microplate clot retraction method, we performed the method in parallel with the Chronolog 700 system using dual (ADP+collagen) and single (Thrombin Receptor Activating Peptide [TRAP]) agonists (n=6). The Area Under Curve (AUC), Slope, and Maximum Amplitude (MaxA) parameters from LTA were evaluated against the six parameters extracted from the microplate clot retraction data. A Principal Component Analysis (PCA) plot, which explained 79% of the total variance, was used to visualize the relationship among all parameters (FIG. 13, which shows principal component analysis variable plot showing the approximate relationship of microplate clot retraction (orange), LTA with TRAP agonist (green), and LTA with ADP+Collagen (purple) parameters.). Not surprisingly, LTA parameters from the same agonist showed strong correlation with each other (FIG. 13, FIG. 14A, and FIG. 14B). In contrast, parameters obtained using different agonists were weakly correlated (FIG. 13, and FIG. 14C through FIG. 14E), possibly due to the strength and concentration of the agonist. FIG. 14 shows correlations among light transmission aggregometry parameters and agonists. In this figure, each sample was analyzed for AUC, MaxA, and Slope after activation with ADP+Collagen and TRAP. Different parameters using the same agonist were strongly correlated; the same parameters using different agonists were weakly correlated.

Comparison of the microplate clot retraction and the LTA parameters by linear regression identified several significant correlations (FIG. 15): (i) Retraction Time showed strong linear relationship with AUC for ADP+Collagen activation ($r^2=0.73$; $p=0.03$), (ii) Retraction Coefficient was moderately correlated with MaxA for ADP+Collagen ($r^2=0.66$; $p=0.04$), (iii) Max. O.D. was strongly correlated with Slope for TRAP ($r^2=0.79$; $p=0.02$), and (iv) Retraction Time and Retraction Coefficient were correlated with MaxA for TRAP ($r^2=0.71$; $p=0.04$ and $r^2=0.78$; $p=0.02$, respectively).

Example 6. Evaluating Stored Platelets Using the Microplate Clot Retraction Method We next tested whether the microplate clot retraction method is able to identify differences in apheresis platelets that were collected in either Platelet Additive Solution (PAS; n=3) or autologous plasma (n=3) and stored for seven days at room temperature with gentle agitation (FIG. 16, which shows the effects of apheresis platelets storage on microplate clot retraction parameters).

Platelets from six donors were collected in either autologous plasma (n=3) or platelet additive solution (PAS; n=3) and assayed on the day of collection (Day 0) or one week of storage at room temperature with agitation (Day 7). In FIG. 16, the bars and error bars depict the mean and SEM, respectively. Differences among groups were analyzed by linear mixed effects models with an interaction term for storage day and solution. F-value and p-values represent the significance of the interaction. Due to censoring, retraction time data were analyzed by the time-to-effect logrank test. Horizontal dashed line shows the assay end-point.

There was a significant effect of storage solution over time for the Rate of Clot Retraction parameter ($p=0.03$) and trends for earlier Time to Max. O.D. and Retraction Time in the PAS stored platelets at day 7 ($p>0.05$).

Example 7. Shelf-Life and Stability of Prepared Microplates

Triplicate wells were prepared in advance according to the timeline in Table 3, below. Each prepared microplate was stored at ambient conditions for temperature and humidity in a closed drawer until the day of use (Day 0). On Day 0, platelet rich plasma (PRP) was prepared from a single donor and an assay according to the invention was performed on wells that were freshly prepared (i.e., Day 0) and wells that were prepared in advance and stored (i.e., Day −43, −36, and −15).

TABLE 3

Timeline of microplate preparation.

| Timeline Date | Day | Phase |
|---|---|---|
| Tuesday 10 Aug. 2021 | −43 | Coat A1-A3 |
| Tuesday 17 Aug. 2021 | −36 | Coat A4-A6 |
| Tuesday 7 Sep. 2021 | −15 | Coat A7-A9 |
| Wednesday 22 Sep. 2021 | 0 | Coat A10-A12; perform assay |

Figure 17:
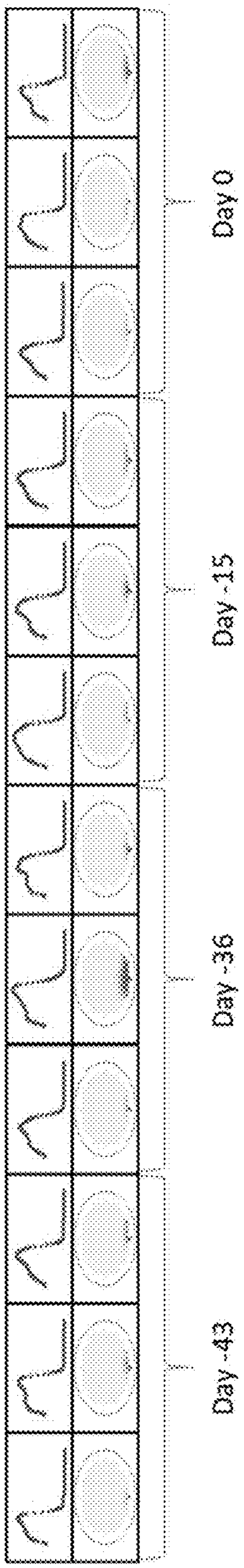
FIG. 17 shows results for the stability of prepared microplates.

Results are shown in FIG. 17, and indicate that advanced preparation and storage of prepared assay plates for up to at least 45 days does not impact performance of the invention.

Example 8. Alternative Method to Prepare Platelets

Whole blood was combined with immunomagnetic particles and red blood cells were removed by negative selection on a magnet. The resulting fluid was depleted for red blood cells (typically $<0.03-0.04\times10^6$ per microliter) but still contained platelets and leukocytes. A side-by-side comparison of platelets prepared using immunomagnetic separation (IMS) and traditional centrifugation (PRP) was made for undiluted and normalized count samples. The experiment was repeated on a second day with a different donor.

Results are shown in FIG. 18 and indicate that IMS preparation of platelets is suitable for use in the methods of this invention. This facilitates sample preparation when centrifugation is not available (e.g., in austere environments).

Example 9. Fluorescent Detection of Clot Retraction

Platelets prepared by centrifugation (PRP) or immunomagnetic separation (IMS) were combined with fluorescent nanoparticles with ex/em wavelengths of 405/450. Two particle sizes were evaluated: 200 nm and 2,000 nm. Results are shown in FIG. 19 shows that fluorescence detection identified clot formation and clot retraction that resembled visible light transmission. The data provided here in the figure was generated using a microplate reader.

Example 10. Optimization of Assay Agonist

Bottom halves of the individual wells in a 96-well plate were coated with 2% Tween and left in a vertical position inside a modified chamber for 90 minutes at room temperature. The coating solutions were then aspirated and allowed to air dry under the hood for 15 minutes. Whole blood collected in ACD tubes from healthy volunteers was subjected to centrifugation at 200×g for 10 minutes to obtain platelet rich plasma (PRP), followed by a second centrifugation at 3000×g for 10 minutes to obtain platelet poor plasma (PPP). When needed, platelet concentrations in the PRP were adjusted to desired levels using PPP. PRP samples (145 μL) were recalcified with 20 mM $CaCl_2$) were then transferred into wells containing five μL of two NIH U/mLs of Thrombin. Further, the changes in absorbance during clot gelation and retraction were tracked at 350 nm using a microplate spectrophotometer for 90 minutes at 37° C.

To evaluate the appropriate thrombin concentration for the best outcome in the assay, we tested at 0.5, 1, 2 and 4 NIH units of thrombin (n=4). Once coagulation was initiated with thrombin, the clotting kinetics were characterized by a very short lag phase of initiation, a log phase of fibrin polymerization, a fibrin densification phase of platelet mediated fibrin remodeling, and a final rapid CR phase of declining absorbance. The onset of retraction occurred between 18 minutes to 21 minutes, with 59% to 46% retraction at 30 minutes compared to 100% CR at 60 minutes after clot initiation with increasing thrombin activity.

Example 11. Effect of Platelet Concentration on Clot Retraction

In order to determine the effect of platelet concentration on the extent of CR, we measured CR in PRP with concentration ranging from 50K to 350K cells/μL with 2U of Thrombin (n=4). A dose dependent increase in retraction was observed, with no retraction at the lowest platelet counts and 41% retraction with 350K platelets/μL at 30 minutes after clot initiation. Similarly, the onset of retraction was highly dependent on the platelet counts with 35±0.5, 29±2.4, 22.5±1.53, 20.7±0.99, 17±0.91 minutes in 50K, 100K, 150K, 200K, 250K, 350K platelets/μL, respectively. Finally, the fibrin densification and rate of CR significantly decreased with the decrease in platelet concentration.

REFERENCES

All references listed below and throughout the specification are hereby incorporated by reference in their entirety.

1. Holcomb J B, del Junco, D J, Fox, E E, Wade, C E, Cohen, M J, Schreiber, M A, Alarcon, L H, Bai, Y, Brasel, K J, Bulger, E M et al. The prospective, observational, multicenter, major trauma transfusion (PROMMTT) study: comparative effectiveness of a time-varying treatment with competing risks. JAMA Surg. 2013; 148:127-136.
2. Holcomb J B, Tilley, B C, Baraniuk, S, Fox, E E, Wade, C E, Podbielski, J M, del Junco, D J, Brasel, K J, Bulger, E M, Callcut, R A et al. Transfusion of plasma, platelets, and red blood cells in a 1:1:1 vs a 1:1:2 ratio and mortality in patients with severe trauma: the PROPPR randomized clinical trial. JAMA. 2015; 313:471-482.
3. Picker S M. In-vitro assessment of platelet function. Transfus Apher Sci. 2011; 44:305-319.
4. Lam W A, Chaudhuri, O, Crow, A, Webster, K D, Li, T D, Kita, A, Huang, JFletcher, D A. Mechanics and contraction dynamics of single platelets and implications for clot stiffening. Nat Mater. 2011; 10:61-66.
5. Tucker K L, Sage, TGibbins, J M. Clot retraction. Methods Mol Biol. 2012; 788:101-107.
6. Tutwiler V, Litvinov, R I, Lozhkin, A P, Peshkova, A D, Lebedeva, T, Ataullakhanov, F I, Spiller, K L, Cines, DBWeisel, J W. Kinetics and mechanics of clot contraction are governed by the molecular and cellular composition of the blood. Blood. 2016; 127:149-159.
7. Li Z, Li, X, McCracken, B, Shao, Y, Ward, KFu, J. A Miniaturized Hemoretractometer for Blood Clot Retraction Testing. Small. 2016; 12:3926-3934.
8. Horn P S, Feng, L, Li, YPesce, A J. Effect of outliers and nonhealthy individuals on reference interval estimation. Clin Chem. 2001; 47:2137-2145.
9. Horn P S, Pesce, AJCopeland, B E. A robust approach to reference interval estimation and evaluation. Clin Chem. 1998; 44:622-631.
10. Ozarda Y. Reference intervals: current status, recent developments and future considerations. Biochem Med (Zagreb). 2016; 26:5-16.
11. Varga-Szabo D, Braun, ANieswandt, B. Calcium signaling in platelets. J Thromb Haemost. 2009; 7:1057-1066.
12. Harrison P, Mackie, I, Mumford, A, Briggs, C, Liesner, R, Winter, M, Machin, SBritish Committee for Standards in, H. Guidelines for the laboratory investigation of heritable disorders of platelet function. Br J Haematol. 2011; 155:30-44.
13. Munnix ICA, Van Oerle, R, Verhezen, P, Kuijper, P, Hackeng, C M, Hopman-Kerkhoff, HIJ, Hudig, F, Van De Kerkhof, D, Leyte, A, De Maat, M P M et al. Harmonizing light transmission aggregometry in the Netherlands by implementation of the SSC-ISTH guideline. Platelets. 2021; 32:516-523.
14. Alessi M C, Sie, PPayrastre, B. Strengths and Weaknesses of Light Transmission Aggregometry in Diagnosing Hereditary Platelet Function Disorders. J Clin Med. 2020; 9:763-781.
15. Moenen F, Vries, MJA, Nelemans, P J, van Rooy, KJM, Vranken, J, Verhezen, PWM, Wetzels, RJH, Ten Cate, H, Schouten, H C, Beckers, E A M et al. Screening for platelet function disorders with Multiplate and platelet function analyzer. Platelets. 2019; 30:81-87.

16. Nair P M, Meledeo, M A, Wells, A R, Wu, X, Bynum, J A, Leung, K P, Liu, B, Cheeniyil, A, Ramasubramanian, A K, Weisel, J W et al. Cold-stored platelets have better preserved contractile function in comparison with room temperature-stored platelets over 21 days. Transfusion. 2021; 61 Suppl 1: S68-S79.
17. Reddoch-Cardenas K M, Peltier, G C, Chance, T C, Nair, P M, Meledeo, M A, Ramasubramanian, A K, Cap, APBynum, J A. Cold storage of platelets in platelet additive solution maintains mitochondrial integrity by limiting initiation of apoptosis-mediated pathways. Transfusion. 2021; 61:178-190.
18. Reddoch-Cardenas K M, Sharma, U, Salgado, C L, Montgomery, R K, Cantu, C, Cingoz, N, Bryant, R, Darlington, D N, Pidcoke, H F, Kamucheka, R M et al. An in vitro pilot study of apheresis platelets collected on Trima Accel system and stored in T-PAS+solution at refrigeration temperature (1-6 degrees C.). Transfusion. 2019; 59:1789-1798.
19. Reddoch-Cardenas K M, Montgomery, R K, Lafleur, C B, Peltier, G C, Bynum, JACap, A P. Cold storage of platelets in platelet additive solution: an in vitro comparison of two Food and Drug Administration-approved collection and storage systems. Transfusion. 2018; 58:1682-1688.
20. Getz™, Montgomery, R K, Bynum, J A, Aden, J K, Pidcoke, HFCap, A P. Storage of platelets at 4 degrees C. in platelet additive solutions prevents aggregate formation and preserves platelet functional responses. Transfusion. 2016; 56:1320-1328.

What is claimed is:

1. A microplate for reading in a microplate reader comprising a series of wells that have been coated with an anti-adherent substance that prevents clot adhesion to a surface and a scored mark on a side of the well in a position configured to be measurable through an optical light path of a detection device.

2. A kit comprising the microplate of claim 1.

3. The kit of claim 2 which further comprises one or more of instructions for performing a clot retraction assay, a thrombin stock solution, a $CaCl_2$) solution, platelet-poor plasma, buffers, and a hand-held or table-top light transmittance detection device.

4. The microplate of claim 1, wherein the scored mark forms an X on the side of the well.

5. The microplate of claim 1, wherein the scored mark is formed on the side of the well at one location around a perimeter of the well.

6. The microplate of claim 1, wherein the scored mark is a groove that has a diameter of about 2-5 millimeters.

7. The microplate of claim 1, wherein the scored mark is a groove with a depth to cause stable clot attachment in the groove upon clot retraction.

8. The microplate of claim 1, wherein the scored mark is formed on the side of the well at the position that corresponds to a meniscus when reagents are placed in the well.

9. The microplate of claim 1, wherein the scored mark on the side of the well is formed by scratching the side of the well with a sharp instrument.

10. The microplate of claim 9, wherein the sharp instrument is an 18 gauge hypodermic needle.

11. The microplate of claim 1, wherein the scored mark is a groove on the side of the well, wherein the groove is configured to accommodate fibrin clot retraction.

12. The kit of claim 3, further comprising the table-top light transmittance detection device that includes a spectrophotometer microplate reader for detection of visible light or fluorescence to make kinetic measurements over a certain wavelength and time.

13. The kit of claim 3, further comprising a sealed container in which the microplate is placed.

14. The kit of claim 3, further comprising blood filters for preparation of platelet rich plasma.

* * * * *